(12) United States Patent
Campbell et al.

(10) Patent No.: US 12,201,556 B2
(45) Date of Patent: Jan. 21, 2025

(54) POROUS STRUCTURES FOR EXTENDED RELEASE DRUG DELIVERY DEVICES

(71) Applicant: ForSight Vision4, Inc., South San Francisco, CA (US)

(72) Inventors: Randolph E. Campbell, South San Francisco, CA (US); Kevin W. Sacherman, South San Francisco, CA (US); Kathleen COgan Farinas, South San Francisco, CA (US); Signe Erickson, South San Francisco, CA (US); Jeremy Boyette, South San Francisco, CA (US)

(73) Assignee: ForSight Vision4, Inc., South San Francisco, CA (US)

( * ) Notice: Subject to any disclaimer, the term of this patent is extended or adjusted under 35 U.S.C. 154(b) by 0 days.

(21) Appl. No.: 17/877,643

(22) Filed: Jul. 29, 2022

(65) Prior Publication Data

US 2023/0072346 A1    Mar. 9, 2023

Related U.S. Application Data

(62) Division of application No. 15/777,593, filed as application No. PCT/US2016/062944 on Nov. 18, 2016, now Pat. No. 11,432,959.

(Continued)

(51) Int. Cl.
*A61F 9/00*    (2006.01)
*A61M 5/142*    (2006.01)

(52) U.S. Cl.
CPC .......... *A61F 9/0017* (2013.01); *A61F 9/0026* (2013.01); *A61F 2250/0067* (2013.01);
(Continued)

(58) Field of Classification Search
CPC ............ A61F 2250/0067; A61F 9/0017; A61F 9/0008; A61F 2250/0068; A61F 2/14;
(Continued)

(56) References Cited

U.S. PATENT DOCUMENTS 1,747,814 A    2/1930    Bradley
2,564,977 A    8/1951    Hu
(Continued)

FOREIGN PATENT DOCUMENTS

CA    2807535 A1    2/2012
CA    2807554 A1    2/2012
(Continued)

OTHER PUBLICATIONS

U.S. Appl. No. 16/091,493, filed Oct. 4, 2018, 2019/0117454.
(Continued)

*Primary Examiner* — Leslie A Lopez
*Assistant Examiner* — Seth Han
(74) *Attorney, Agent, or Firm* — Mintz Levin Cohn Ferris Glovsky and Popeo, P.C.

(57) ABSTRACT

A therapeutic device for extended release drug delivery including a refillable reservoir configured to receive a therapeutic agent and having an outlet for delivery of the therapeutic agent to a patient from the reservoir over an extended period. A porous structure is coupled near the outlet of the reservoir, the porous structure formed of sintered material. A barrier layer is coupled to the reservoir on or adjacent a surface of the porous structure such that the therapeutic agent passes through both the porous structure and the barrier layer upon delivery from the reservoir through the outlet. The porous structure is tuned to deliver the therapeutic agent at a diffusion rate and the barrier layer is adapted to block passage of particles having an average particle size within an average particle size range that is outside an (Continued)

average particle size range blocked by the porous structure. Related methods and systems are provided.

12 Claims, 13 Drawing Sheets

Related U.S. Application Data

(60) Provisional application No. 62/258,127, filed on Nov. 20, 2015, provisional application No. 62/258,054, filed on Nov. 20, 2015.

(52) U.S. Cl.
CPC .. *A61F 2250/0068* (2013.01); *A61M 5/14276* (2013.01); *A61M 2205/04* (2013.01); *A61M 2205/125* (2013.01); *A61M 2205/75* (2013.01)

(58) Field of Classification Search
CPC ............... A61F 2/147; A61M 2205/75; A61M 2205/02; A61M 5/14276; A61M 2205/04; A61M 31/002; A61M 2205/125; A61M 2205/126; A61K 9/0051; A61B 5/4839; A61B 5/686; A61J 1/1412; A61J 1/1468
See application file for complete search history.

(56) References Cited

U.S. PATENT DOCUMENTS

| | | |
|---|---|---|
| 2,585,815 A | 2/1952 | Mclintock |
| 2,886,497 A | 5/1959 | Butler |
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,826,258 A | 7/1974 | Abraham |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shel |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,986,510 A | 10/1976 | Higuchi et al. |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,577,642 A * | 3/1986 | Stokes ............... A61N 1/0568 424/425 |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,710,167 A | 12/1987 | Lazorthes |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,781,680 A | 11/1988 | Redmond et al. |
| 4,840,615 A | 6/1989 | Hancock et al. |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,013,459 A | 5/1991 | Gettings et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,197,882 A | 3/1993 | Jernberg |
| 5,219,101 A * | 6/1993 | Matkovich ............. B65D 47/18 210/321.64 |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,516,522 A | 5/1996 | Peyman et al. |
| 5,554,132 A | 9/1996 | Straits et al. |
| 5,562,915 A | 10/1996 | Lowe et al. |
| 5,576,480 A | 11/1996 | Hopkins et al. |
| 5,681,572 A | 10/1997 | Seare, Jr. |
| 5,702,414 A | 12/1997 | Richter et al. |
| 5,704,915 A | 1/1998 | Melsky et al. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,492 A | 11/1998 | Usala |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |

(56) References Cited

U.S. PATENT DOCUMENTS

| | | |
|---|---|---|
| 5,985,328 A | 11/1999 | Chu et al. |
| 5,989,216 A | 11/1999 | Johnson et al. |
| 6,001,386 A | 12/1999 | Ashton et al. |
| 6,096,070 A | 8/2000 | Ragheb et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,361,780 B1 | 3/2002 | Ley et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,003,405 B1 | 2/2006 | Ho |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,117,870 B2 | 10/2006 | Prescott |
| 7,141,023 B2 | 11/2006 | Diermann et al. |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 8,304,524 B2 | 11/2012 | Bairstow et al. |
| 8,399,006 B2 | 3/2013 | de Juan, Jr. et al. |
| 8,439,865 B2 | 5/2013 | Lust et al. |
| 8,486,052 B2 | 7/2013 | Varner et al. |
| 8,623,395 B2 | 1/2014 | de Juan, Jr. et al. |
| 8,795,712 B2 | 8/2014 | de Juan, Jr. et al. |
| 8,808,727 B2 | 8/2014 | de Juan, Jr. et al. |
| 9,033,911 B2 | 5/2015 | de Juan, Jr. et al. |
| 11,432,959 B2 * | 9/2022 | Campbell ............ A61F 9/0026 |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0133154 A1 | 7/2004 | Flaherty et al. |
| 2004/0171997 A1 | 9/2004 | Wilson et al. |
| 2004/0199128 A1 | 10/2004 | Morris et al. |
| 2004/0208910 A1 | 10/2004 | Ashton et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0118229 A1 * | 6/2005 | Boiarski ............ A61K 9/0024 424/424 |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0255144 A1 | 11/2005 | Schultz |
| 2005/0256499 A1 | 11/2005 | Pettis et al. |
| 2005/0267440 A1 | 12/2005 | Herman et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0020253 A1 | 1/2006 | Prescott |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0088335 A1 | 4/2007 | Jolly |
| 2007/0088414 A1 | 4/2007 | Campbell et al. |
| 2007/0088432 A1 | 4/2007 | Solovay et al. |

(56) References Cited

U.S. PATENT DOCUMENTS

| | | |
|---|---|---|
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0156079 A1* | 7/2007 | Brown .................. A61B 3/16 604/9 |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford, et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0027304 A1 | 1/2008 | Pardo et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0269318 A1 | 10/2008 | Romano |
| 2008/0286338 A1 | 11/2008 | Rosenthal et al. |
| 2008/0292679 A1 | 11/2008 | Lyons et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0061071 A1 | 3/2009 | McMorrow et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306595 A1 | 12/2009 | Shih et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0075950 A1 | 3/2010 | Gant et al. |
| 2010/0083963 A1 | 4/2010 | Wharton et al. |
| 2010/0100043 A1 | 4/2010 | Racenet |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0076278 A1 | 3/2011 | Khodadoust |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |

(56) References Cited

U.S. PATENT DOCUMENTS

| | | |
|---|---|---|
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2011/0208122 A1 | 8/2011 | Shekalim |
| 2012/0029445 A1 | 2/2012 | de Juan, Jr. et al. |
| 2012/0029470 A1 | 2/2012 | Juan, Jr. et al. |
| 2012/0095439 A1 | 4/2012 | de Juan, Jr. et al. |
| 2012/0183799 A1 | 7/2012 | Steele et al. |
| 2012/0184905 A1 | 7/2012 | Shekalim |
| 2013/0165860 A1 | 6/2013 | Doud et al. |
| 2013/0218081 A1 | 8/2013 | Roth |
| 2013/0245573 A1 | 9/2013 | de Juan, Jr. et al. |
| 2013/0274691 A1 | 10/2013 | de Juan, Jr. et al. |
| 2013/0274692 A1 | 10/2013 | Alster et al. |
| 2013/0304031 A1 | 11/2013 | Varner et al. |
| 2013/0324942 A1 | 12/2013 | de Juan, Jr. et al. |
| 2014/0031769 A1 | 1/2014 | de Juan, Jr. et al. |
| 2014/0033800 A1 | 2/2014 | Farinas et al. |
| 2014/0073714 A1 | 3/2014 | Reich et al. |
| 2014/0121609 A1 | 5/2014 | de Juan, Jr. et al. |
| 2014/0221941 A1 | 8/2014 | Erickson et al. |
| 2014/0243795 A1 | 8/2014 | Varner et al. |
| 2014/0276482 A1 | 9/2014 | Astafieva et al. |
| 2014/0296800 A1* | 10/2014 | Erickson ............... A61F 9/0017 604/288.02 |
| 2014/0299125 A1 | 10/2014 | Buchberger |
| 2014/0358125 A1 | 12/2014 | de Juan, Jr. et al. |
| 2015/0080846 A1 | 3/2015 | de Juan, Jr. et al. |
| 2015/0297402 A1 | 10/2015 | de Juan, Jr. et al. |
| 2016/0038488 A1 | 2/2016 | Horvath et al. |
| 2016/0101046 A1 | 4/2016 | Reich et al. |
| 2016/0128867 A1 | 5/2016 | Bachelder et al. |
| 2016/0184134 A1 | 6/2016 | Varner et al. |
| 2016/0258855 A1 | 9/2016 | Farinas et al. |
| 2016/0302965 A1 | 10/2016 | Erickson et al. |
| 2017/0165108 A1 | 6/2017 | Bianchi et al. |
| 2017/0165110 A1 | 6/2017 | Erickson et al. |
| 2017/0172794 A1 | 6/2017 | Varner et al. |
| 2017/0258634 A1 | 9/2017 | de Juan, Jr. et al. |
| 2018/0147204 A1 | 5/2018 | Horvath et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |
| 2018/0289542 A1 | 10/2018 | de Juan, Jr. et al. |
| 2018/0292403 A1 | 10/2018 | de Juan, Jr. et al. |
| 2019/0117454 A1 | 4/2019 | Campbell et al. |
| 2020/0337897 A1 | 10/2020 | Sacherman et al. |

FOREIGN PATENT DOCUMENTS

| | | |
|---|---|---|
| CN | 1585627 A | 2/2005 |
| CN | 101052435 A | 10/2007 |
| CN | 101437478 A | 5/2009 |
| CN | 101448534 A | 6/2009 |
| CN | 102762746 A | 10/2012 |
| EP | 0033042 B1 | 8/1984 |
| EP | 0 228 185 A1 | 11/1986 |
| EP | 0498471 | 8/1992 |
| EP | 0500143 | 8/1992 |
| EP | 0295248 | 3/1993 |
| EP | 0671165 | 9/1995 |
| EP | 0944658 B1 | 6/2003 |
| EP | 1671624 | 6/2006 |
| EP | 1385452 | 9/2006 |
| EP | 1409065 | 1/2007 |
| EP | 1337284 B1 | 12/2007 |
| EP | 1911481 | 4/2008 |
| EP | 1521572 B1 | 3/2009 |
| JP | 2004-524866 A | 8/2004 |
| JP | 2005-500097 A | 1/2005 |
| JP | 2006-526430 A | 11/2006 |
| JP | 2013-523283 A | 6/2013 |
| WO | WO-88/04573 A1 | 6/1988 |
| WO | WO-90/07545 A2 | 7/1990 |
| WO | WO-95/28984 A1 | 11/1995 |
| WO | WO-97/29850 | 8/1997 |
| WO | WO-98/25982 | 6/1998 |
| WO | WO-98/43611 A1 | 10/1998 |
| WO | WO-99/11244 | 3/1999 |
| WO | WO-00/48660 | 8/2000 |
| WO | WO-01/26714 | 4/2001 |
| WO | WO-01/50943 | 7/2001 |
| WO | WO-01/68016 A2 | 9/2001 |
| WO | WO-02/017831 A2 | 3/2002 |
| WO | WO-02/053128 A2 | 7/2002 |
| WO | WO-02/100318 | 12/2002 |
| WO | WO-03/028765 | 4/2003 |
| WO | WO-03/077972 | 9/2003 |
| WO | WO-03/082188 | 10/2003 |
| WO | WO-2004/000267 | 12/2003 |
| WO | WO-2004/073765 A2 | 9/2004 |
| WO | WO-2004/098565 A2 | 11/2004 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 A2 | 11/2005 |
| WO | WO-2005/110473 A2 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/050221 | 5/2006 |
| WO | WO-2006/068838 | 6/2006 |
| WO | WO-2006/071554 A2 | 7/2006 |
| WO | WO-2006/082588 A2 | 8/2006 |
| WO | WO-2006/108054 | 10/2006 |
| WO | WO-2006/127962 | 11/2006 |
| WO | WO-2006/138609 | 12/2006 |
| WO | WO-2007/002184 A1 | 1/2007 |
| WO | WO-2007/012974 | 2/2007 |
| WO | WO-2007/035473 | 3/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO-2007/066339 | 6/2007 |
| WO | WO-2007/084582 | 7/2007 |
| WO | WO-2007/084765 | 7/2007 |
| WO | WO-2007/101204 | 9/2007 |
| WO | WO-2007/115259 A2 | 10/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/019265 | 2/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 | 5/2008 |
| WO | WO-2008/076544 | 6/2008 |
| WO | WO-2008/094989 A2 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |

(56) References Cited

FOREIGN PATENT DOCUMENTS

| WO | WO-2009/055671 | 4/2009 |
|---|---|---|
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010/075565 | 7/2010 |
| WO | WO-2010/078063 | 7/2010 |
| WO | WO-2010/088548 A1 | 8/2010 |
| WO | WO-2010/093945 | 8/2010 |
| WO | WO-2010/095940 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/079232 | 6/2011 |
| WO | WO-2012/019047 A2 | 2/2012 |
| WO | WO-2012/019136 A2 | 2/2012 |
| WO | WO-2012/065006 A2 | 5/2012 |
| WO | WO-2016/022750 A1 | 2/2016 |

OTHER PUBLICATIONS

U.S. Appl. No. 16/386,854, filed Apr. 17, 2019, 2019/0336335.
U.S. Appl. No. 16/540,617, filed Aug. 14, 2019, 2020/0030142.
U.S. Appl. No. 16/808,784, filed Mar. 4, 2020, 2020/0405537.
U.S. Appl. No. 16/842,059, filed Apr. 7, 2020, 2021/0025885.
U.S. Appl. No. 17/016,953, filed Sep. 10, 2020, 2021/0196510.
U.S. Appl. No. 17/393,059, filed Aug. 3, 2021, 2022/0087863.
U.S. Appl. No. 17/745,007, filed May 16, 2022, 2022/0378609.
"MAbPac SCX-10 Column for Monoclonal Antibody Variant Analysis." *Dionex.* Aug. 2010. 4 pages. [http://www.dionex.com/en-us/webdocs/87008-DS-MAbPac-SCX-10-Column-20Aug2010-LPN2567-03.pdf]. Web. Retrieved May 2012.
Andrews, "Effect of nonsteroidal anti-inflammatory drugs on LFA-1 and ICAM-1 expression in gastric mucosa," Am J Physiol. Apr. 1994;266 (4 Pt 1): G657-664.
ASTM Designation: E 128-99. Standard Test Method for Maximum Pore Diameter and Permeability of Rigid Porous Filters for Laboratory Use. Aug. 1999. Retrieved Jul. 4, 2014. 3 pages.
Avery et al., "Intravitreal bevacizumab (Avastin) in the treatment of proliferative diabetic retinopathy," Ophthalmology. Oct. 2006; 113(10):1695-1705.e6.
Bakri et al., "The effect of intravitreal triamcinolone acetonide on intraocular pressure," Ophthalmic Surgery, Lasers and Imaging, Sep./Oct. 2003; 34(5): 386-390.
Bird et al., Transport Phenomena, John Wiley & Sons, Inc., New York, 1960, pp. 196-201.
Block et al., "Solubility and dissolution of triamcinolone acetonide," Journal of Pharmaceutical Sciences, Apr. 1973; 62(4):617-621.
Carbonaro, et al. "Nano-pore silicon membrane characterization by diffusion and electrical resistance." *Journal of Membrane Science.* 241 (2004):249-255.
Castro et al., "Effect of COX inhibitors on VEGF-induced retinal vascular leakage and experimental corneal and choroidal neovascularization," Exp Eye Res. Aug. 2004;79(2):275-285.
Chirila et al., "The Vitreous Humor" in *Handbook of Biomaterial Properties,* eds. Black & Hastings. Chapman & Hall, London, 1998; pp. 125-131.
Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.
Deissler et al., "VEGF-induced effects on proliferation, migration and tight junctions are restored by ranibizumab (Lucentis) in microvascular retinal endothelial cells," Br J Ophthalmol 2008;92:839-843.
Donoso et al., "The role of inflammation in the pathogenesis of age-related macular degeneration," Surv Ophthalmol. Mar.-Apr. 2006;51(2):137-52.
European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.
Funatsu et al. "Association of vitreous inflammatory factors with diabetic macular edema," Ophthalmology 2009;116:73-79.
Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.
Gillies et al., "Intravitreal triamcinolone for refractory diabetic macular edema: two-year results of a double-masked, placebo-controlled, randomized clinical trial," Ophthalmology. Sep. 2006;113(9):1533-1538.
Grattoni et al. "Analysis of a nanochanneled membrane structure through convective gas flow." *J. Micromech. Microeng.* 19 (2009). 115018 (11pp).
Hastedt & Wright, "Diffusion in porous materials above the percolation threshold," Pharm. Res. Sep. 1990; 7(9):893-901 (1990).
Heier et al., "Ketorolac versus prednisolone versus combination therapy in the treatment of acute pseudophakic cystoid macular edema," Ophthalmology. Nov. 2000;107(11):2034-2038 ;discussion 2039.
Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.
Jornitz et al. "Filter Integrity Testing in Liquid Applications, Revisited; Part 1." *Pharmaceutical Technology.* Oct. 2001. pp. 34-50.
Kang et al., "Inhibitory effects of anti-inflammatory drugs on interleukin-6 bioactivity," Biol Pharm Bull. Jun. 2001;24(6):701-703.
Lopez-Armada et al., "Modulation of cell recruitment by anti-inflammatory agents in antigen-induced arthritis," Ann Rheum Dis Nov. 2002;61(11):1027-1030.
Luncentis, INN-Ranibizumab, "Scientific Discussion," European Medicines Agency. Retrieved from the Internet: <http://www.ema.europa.eu/docs/en_GB/document_library/EPAR_-_Assessment_Report_-_Variation/human/000715/WC500101009.pdf>. Oct. 21, 2010. 32 pages.
Metal Powder Industries Federation, Porous Metal Design Guidebook, 2007, 24 pages total. Downloaded from the Internet: <<http://www.mpif.org/DesignCenter/porous.pdf>>.
Millipore. "Filter Integrity Test Methods." Millipore Corporation. 1999. 12 pages.
Molokhia et al., "Transscleral iontophoretic and intravitreal delivery of a macromolecule: Study of ocular distribution in vivo and postmortem with MRI", Experimental Eye Research 88 (2009) 418-425.
MOTT Corporation, "Sintered Metal Powder Media," American Filtration & Separation Society 2007, 2 pages total. Downloaded from the Internet:<<http://www.afssociety.org/education/0907oneminute.htm>>.

(56) References Cited

OTHER PUBLICATIONS

Navarro, "The Optical Design of the Human Eye: a Critical Review," J Optom, Jan.-Mar. 2009 2(1): 3-18.

Nutan, M.T.H. et al. (2010) "General Principles of Suspensions," Chapter 2 in Pharmaceutical Suspensions From Formulation Development to Manufacturing, editors AK Kulshreshtha, et al., Spinger. 29 pages.

Okabe et al., "Intraocular tissue distribution of betamethasone after intrascleral administration using a non-biodegradable sustained drug delivery device," Investigative Ophthalmology and Visual Science. 2003;44: 2702-2707. Downloaded from the Internet: <<http://www.iovs.org/cgi/reprint/44/6/2702>>.

Rosenfeld, "The Latest Research: Intravitreal Bevacizumab for Proliferative Diabetic Retinopathy," Review of Ophthalmology's Retina Online, Feb. 2006; 2 pages. Retrieved from the Internet: http://www.revophth.com/archive/newsletter/0206_retina.htm.

Smith et al., "Spectrophotometric determination of pKa values for fluorescein using activity coefficient corrections," WaterSA 2002; 28(4):395-402.

Soheilian et al., "Pilot Study of Intravitreal Injection of Diclofenac for Treatment of Macular Edema of Various Etiologies," Retina, Mar. 2010; 30(3): 509-515.

Stay et al. Computer Simulation of Convective and Diffusive Transport of Controlled-Release Drugs in the vitreous Humor, *Pharm Res* 2003,20(1), pp. 96-102.

Theodossiadis et al., "Intravitreal administration of the anti-tumor necrosis factor agent infliximab for neovascular age-related macular degeneration," Am J Ophthalmol. May 2009;147(5):825-830.

Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.

\* cited by examiner

POROUS STRUCTURES FOR EXTENDED RELEASE DRUG DELIVERY DEVICES

CROSS-REFERENCE TO RELATED APPLICATIONS

This application claims priority to U.S. Provisional Application Nos. 62/258,054, filed Nov. 20, 2015, entitled "Porous Structures for Extended Release Drug Delivery Devices;" and 62/258,127, filed Nov. 20, 2015, entitled "Porous Structures for Extended Release Drug Delivery Devices," the entire contents of which are hereby incorporated by reference herein in their entireties.

FIELD

The present technology relates generally to extended release drug delivery devices and more particularly, to porous structures for extended release drug delivery devices.

BACKGROUND

Implantable devices are used to deliver therapeutic agents to a variety of tissues for an extended period of time. Some implanted devices do not provide sustained release of the therapeutic agent for the desired extended period or at the desired therapeutic level. Some of the known implanted devices may rely on polymer membranes or polymer matrices to control the rate of drug release, and many of the known membranes and matrices may he incompatible with at least some therapeutic agents such as ionic drugs and large molecular weight protein drugs in at least some instances. At least some of the known semi-permeable polymer membranes may have permeability that is less than ideal for the extended release of large molecular weight proteins such as antibodies or antibody fragments. At least some of the known semi-permeable membranes can have a permeability of large molecules that may vary over time and at least some of the known semi-permeable membranes can be somewhat fragile, such that drug release for extended periods can be less than ideal in at least some instances. At least some of the proposed devices that rely on pores and capillaries may allow microbes such as bacteria to pass through the capillary and/or pore, such that infection may be spread. At least some of the proposed implanted devices do not provide adequate protection from the patient's immune system, such as from macrophages and antibodies, thereby limiting the therapeutic effect in at least some instances.

In light of the above, it would be desirable to provide improved therapeutic devices and methods that overcome at least some of the above deficiencies of the known therapies, for example with improved drug release that can be maintained when implanted over an extended time.

SUMMARY

In an aspect, described is a therapeutic device for extended release drug delivery including a refillable reservoir configured to receive a therapeutic agent and having an outlet for delivery of the therapeutic agent to a patient from the reservoir over an extended period. A porous structure is coupled near the outlet of the reservoir, the porous structure formed of sintered material. A barrier layer is coupled to the reservoir on or adjacent a surface of the porous structure such that the therapeutic agent passes through both the porous structure and the barrier layer upon delivery from the reservoir through the outlet. The porous structure is tuned to deliver the therapeutic agent at a diffusion rate and the barrier layer is adapted to block passage of particles having an average particle size within an average particle size range that is outside an average particle size range blocked by the porous structure.

The average particle size range blocked by the barrier layer can be greater than about 0.01 um or greater than about 1 nm. The porous structure can have a mean pore size that is between about 3 microns to about 50 microns. The barrier layer can have a mean pore size that is between about 0.01 microns to about 0.1 microns. The surface of the porous structure can be one or both of an inner-facing surface of the porous structure and an outer-facing surface of the porous structure, the inner-facing surface facing the reservoir and the outer-facing surface is on an external side of the reservoir. The barrier layer can be coupled within the reservoir and can be spaced a distance proximal to the inner facing surface of the porous structure. The barrier layer can be a filter membrane formed of silver metal, cellulose acetate, ceramic, glass fiber, borosilicate fiber, mixed cellulose ester (MCE), nylon, polyacrylonitrile (PAN), polycarbonate track etch (PCTE), polyethersulfone (PES), polyester track etch (PETE), polypropylene (PP), PTFE, or PVDF. The sintered material of the porous structure can be stainless steel or titanium.

The porous structure can have pores having a first mean pore size and the barrier layer can be a filter membrane having pores of a second mean pore size. The first mean pore size can be equal to or greater than the second mean pore size. A diffusion rate of the therapeutic agent through the porous structure in the presence of the filter membrane can be substantially the same as the diffusion rate of the therapeutic agent through the porous structure in absence of the filter membrane. The second mean pore size can be effective to block passage of the particles having the average particle size within the average particle size range. The average particle size range of the barrier layer can be equal to or smaller than 0.2 microns and greater than an average particle size range of the therapeutic agent. The particles blocked by the barrier layer can include one or more microbes, bacteria, fungal spores, immune cells, or antibodies. The porous structure can have a first porosity and the barrier layer can have a second porosity. The first porosity can be higher than the second porosity. The first porosity can be from about 16% to about 30% and the second porosity can be from about 1% to about 15%. The porous structure can have a thickness from about 70 microns to about 5000 microns and the barrier layer can have a thickness from about 10 nm to about 150 microns. The barrier layer can mitigate a bolus release of the therapeutic agent through the porous structure upon application of a positive pressure within the reservoir.

In an interrelated aspect, provided is a therapeutic device for extended release drug delivery including a refillable reservoir configured to receive a therapeutic agent and having an outlet for delivery of the therapeutic agent to a patient from the reservoir. A porous structure is coupled near the outlet of the reservoir and is formed of sintered material. A barrier layer is coupled to the reservoir on or adjacent a surface of the porous structure such that the therapeutic agent passes through both the porous structure and the barrier layer upon delivery from the reservoir through the outlet. The barrier layer is configured to block passage of contaminants from entering the eye through the porous structure, or is configured to block passage of contaminants from entering the reservoir through the porous structure, or is configured to block passage contaminants from entering the eye and the reservoir through the porous structure. The contaminants can include one or more of microbes, bacteria, fungal spores, immune cells, and antibodies. The barrier layer can mitigate bolus release of the therapeutic agent upon an increase in pressure within the reservoir.

In an interrelated aspect, provided is a therapeutic device for extended release drug delivery including a refillable reservoir configured to receive one or more therapeutic agents and having an outlet for delivery of the therapeutic agent to a patient from the reservoir. A porous structure is coupled to the reservoir near the outlet from the reservoir. The porous structure is formed of sintered material and has a first porosity and a first mean pore size. A barrier layer is coupled to the reservoir on or adjacent a surface of the porous structure such that the therapeutic agent passes through both the porous structure and the barrier layer upon delivery from the reservoir through the outlet. The barrier layer is a filter membrane having a second porosity and a second mean pore size. The first porosity is greater than the second porosity and the first mean pore size is equal to or greater than the second mean pore size.

In an interrelated aspect, provided is a method of manufacturing a therapeutic device for extended release drug delivery. The method includes selecting a first porous structure having specified characteristics including a porosity (P), a surface area (A), a tortuosity (T), and a thickness (L), wherein the specified characteristics affect molecular diffusion rate of molecules through the first porous structure according to a release rate index=PA/TL. The method includes performing a non-destructive test on the first porous structure to obtain a performance result. The non-destructive test is a gas flow rate test, a bubble point test, or a pressure decay test. The method includes measuring a diffusion rate of a molecule through a second porous structure according to passive, concentration-gradient driven molecular diffusion to obtain a measured diffusion rate. The second porous structure has the same specified characteristics as the first porous structure. The method includes correlating the performance result to the measured diffusion rate to form a correlation. The method includes predicting a measured diffusion rate of the molecule through at least a third porous structure having the specified characteristics using the correlation.

The first porous structure and the second porous structure can be the same porous structure or can be different porous structures. The method can further include forming a porous coating on a porous structure having the specified characteristics. Forming a porous coating can include (a) forming a suspension of sinterable particles in a carrier fluid; (b) coating the porous structure with the suspension using an ultrasonic spray nozzle; and (c) sintering the sinterable particles to the porous structure forming a coated porous structure. The sinterable particles can be stainless steel particles having an average particle size of from 50 nanometers to 350 nanometers. The method can further include performing the non-destructive test on the coated porous structure to obtain a coated structure performance result. The method can further include determining whether the coated structure performance result is significantly different from the performance result of the first porous structure. The method can further include measuring a diffusion rate of the molecule through the coated porous structure to obtain a coated structure diffusion rate. The method can further include predicting a measured diffusion rate of the molecule through the coated porous structure based on the coated structure performance result.

In an interrelated aspect, disclosed is a therapeutic device for extended release drug delivery having a refillable reservoir configured to hold one or more therapeutic agents and having an outlet for delivery of the one or more therapeutic agents to a patient from the reservoir. A porous structure is coupled to the reservoir near the outlet. The porous structure is formed of sintered material and has a first porosity and a first mean pore size. A barrier layer is on or adjacent a surface of the porous structure such that the one or more therapeutic agents pass through both the porous structure and the barrier layer upon delivery from the reservoir through the outlet. The barrier layer has a second porosity and a second mean pore size. The first porosity is greater than the second porosity and the first mean pore size is equal to or greater than the second mean pore size. The barrier layer is formed of a coating of stainless steel particles or a coating of titanium particles sintered to the surface of the porous structure.

The surface of the porous structure can be one or both of an inner-facing surface of the porous structure and an outer-facing surface of the porous structure, the inner-facing surface facing the reservoir and the outer-facing surface is on an external side of the reservoir. The first mean pore size of the porous structure can be between about 3 microns to about 50 microns. A diffusion rate of the one or more therapeutic agents through the porous structure having the barrier layer can be substantially the same as a diffusion rate of the one or more therapeutic agents through the porous structure in absence of the barrier layer. The second mean pore size can be effective to block passage of the second size molecule. The second size molecule can be equal to or greater than 0.2 microns. The second mean pore size can be 0.2 microns. The barrier layer can block passage of a second size molecule to inhibit the second size molecule from passing from the reservoir to outside the device. The second size molecule can be one or more microbes or other contaminants described herein. The barrier layer can block passage of a second size molecule to inhibit the second size molecule from passing into the reservoir from outside the device. The second size molecule can include one or more microbes or immune cells or other contaminants. The first porosity can be from about 16% to about 30% and the second porosity can be from about 1% to about 15%. The porous structure can have a thickness from about 70 microns to about 5000 microns and the barrier layer can have a thickness from about 10 nm to about 150 microns. The barrier layer can mitigate a bolus release of the one or more therapeutic agents through the porous structure upon application of a positive pressure within the reservoir.

In an interrelated aspect, disclosed is a method of manufacturing a therapeutic device for extended release drug delivery including selecting a first porous structure having specified characteristics including a titanium particle size, a porosity and a thickness; performing a non-destructive test on the first porous structure to obtain a performance result. The non-destructive test is a gas flow rate test, a bubble point test, or a pressure decay test. The method includes measuring a diffusion rate of a molecule through a second porous structure according to passive, concentration-gradient driven molecular diffusion to obtain a measured diffusion rate. The second porous structure has the same specified characteristics as the first porous structure. The method includes correlating the performance result to the measured diffusion rate to form a correlation; and predicting a measured diffusion rate of the molecule through at least a third porous structure having the specified characteristics using the correlation.

The first porous structure and the second porous structure can be the same porous structure or can be different porous structures. The method can further include forming a porous coating on a porous structure having the specified characteristics comprises depositing a thin film titanium coating on the porous structure using plasma enhanced chemical vapor deposition to obtain a coated porous structure. The method can further include performing the non-destructive test on the coated porous structure to obtain a coated structure performance result. The method can further include determining whether the coated structure performance result is significantly different from the performance result of the first porous structure. The method can further include measuring a diffusion rate of the molecule through the coated porous structure to obtain a coated structure diffusion rate. The method can further include predicting a measured diffusion rate of the molecule through the coated porous structure based on the coated structure performance result.

in some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

DETAILED DESCRIPTION

Figure 1:
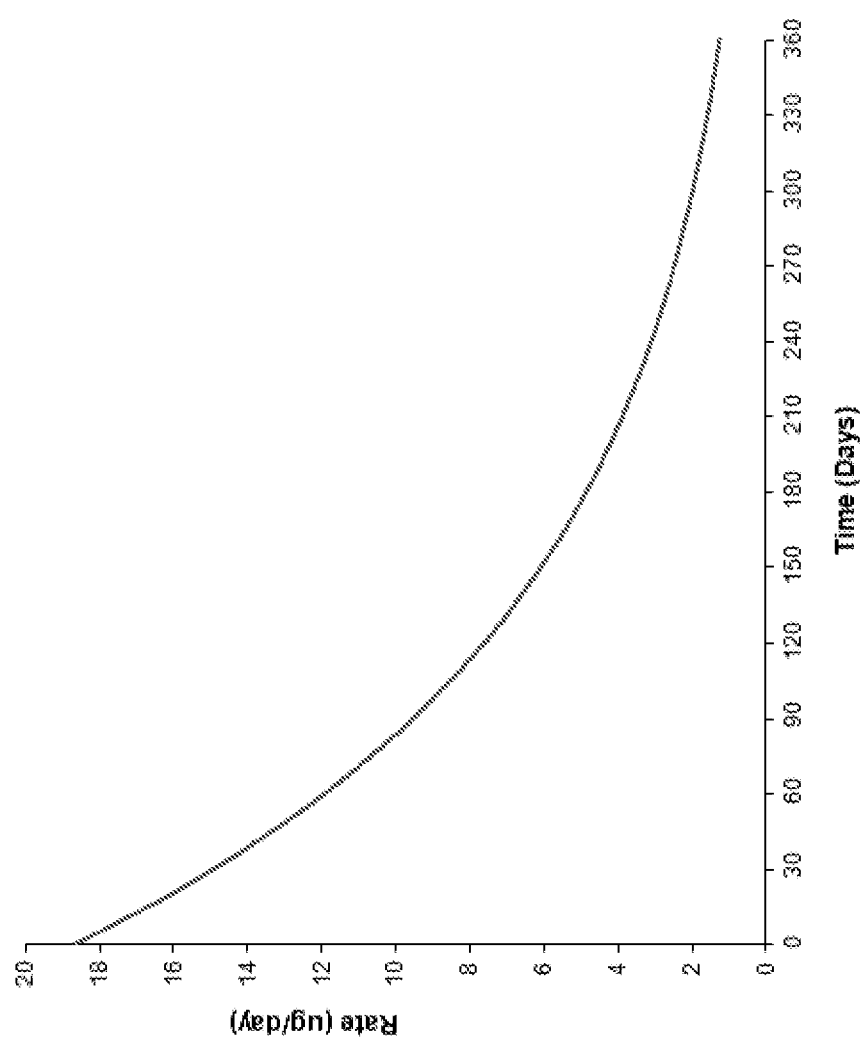
FIG. 1 illustrates a hypothetical example of a Fickian release profile.

Described herein are therapeutic devices for extended release drug delivery. The devices include one or more porous structures for the delivery of one or more therapeutics for the treatment of diseases. The devices and systems described herein can deliver therapeutics to select regions and structures of the body over a variety of periods of time. The therapeutic devices and systems described herein can be used for extended release drug delivery of one or more therapeutic agents. The therapeutic device can include a refillable reservoir configured to receive a bolus injection the therapeutic agent(s). The reservoir can have an outlet for delivery of the bolus injection of the therapeutic agent(s) to a patient from the reservoir over an extended period of time. The device can include a porous structure coupled near the outlet of the reservoir. The porous structure can be formed of a sintered material and will be described in more detail below. The device can include a barrier layer coupled to the reservoir on or adjacent a surface of the porous structure such that the therapeutic agent passes through both the porous structure and the barrier layer upon delivery from the reservoir through the outlet. The porous structure is tuned to deliver the therapeutic agent at a predetermined diffusion rate and the barrier layer is adapted to retain particles having an average particle size range that is different from or outside the average particle size range retained by the porous structure. Thus, the barrier layer is configured to block passage of contaminants from entering the eye through the porous structure, or block passage of contaminants from entering the reservoir through the porous structure, or both. The contaminants can vary including, for example, one more microbes, bacteria, fungal spores, immune cells, cellular products such as antibodies. The barrier layer can also mitigate bolus release of the therapeutic agent upon an increase in pressure within the reservoir.

Unless defined otherwise, all technical and scientific terms used herein have the same meaning as is commonly understood by one of skill in the art. All patents, patent applications, published applications and publications, websites and other published materials referred to throughout the entire disclosure herein, unless noted otherwise, are incorporated by reference in their entirety. In the event that there are pluralities of definitions for terms herein, those in this section prevail. Where reference is made to a URL or other such identifier or address, it is understood that such identifiers can change and particular information on the internet can come and go. but equivalent information is known and can be readily accessed, such as by searching the internet and/or appropriate databases. Reference thereto evidences the availability and public dissemination of such information.

As used herein, relative directional terms such as anterior, posterior, proximal, distal, lateral, medial, sagittal, coronal, transverse, etc. are used throughout this disclosure. Such terminology is for purposes of describing devices and features of the device and is not intended to be limited. For as used herein "proximal" generally means closest to a user implanting a device and farthest from the target location of implantation, while "distal" means farthest from the user implanting a device in a patient and closest to the target location of implantation.

As used herein, a disease or disorder refers to a pathological condition in an organism resulting from, for example, infection or genetic defect, and characterized by identifiable symptoms.

As used herein, treatment means any manner in which the symptoms of a condition, disorder or disease are ameliorated or otherwise beneficially altered. Treatment also encompasses any pharmaceutical use of the devices described and provided herein.

As used herein, amelioration or alleviation of the symptoms of a particular disorder, such as by administration of a particular pharmaceutical composition, refers to any lessening, whether permanent or temporary, lasting or transient that can be attributed to or associated with administration of the composition.

As used herein, an effective amount of a compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms. Pharmaceutically effective amount, therapeutically effective amount, biologically effective amount and therapeutic amount are used interchangeably herein to refer to an amount of a therapeutic that is sufficient to achieve a desired result, i.e. therapeutic effect, whether quantitative or qualitative. In particular, a pharmaceutically effective amount, in vivo, is that amount that results in the reduction, delay, or elimination of undesirable effects (such as pathological, clinical, biochemical and the like) in the subject.

As used herein, sustained release encompasses release of effective amounts of an active ingredient of a therapeutic agent for an extended period of time. The sustained release may encompass first order release of the active ingredient, zero order release of the active ingredient, or other kinetics of release such as intermediate to zero order and first order, or combinations thereof. The sustained release may encompass controlled release of the therapeutic agent via passive molecular diffusion driven by a concentration gradient across a porous structure.

As used herein, a subject includes any animal for whom diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

As used herein, a therapeutic agent referred to with a trade name encompasses one or more of the formulation of the therapeutic agent commercially available under the trade name, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

As used herein, a composition refers to any mixture. It can be a solution, a suspension, an emulsion, liquid, powder, a paste, aqueous, non-aqueous or any combination of such Ingredients.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination, optionally, including instructions for use of the combination and/or other reactions and components for such use.

As used herein, "nano", "nano-sized", "nano-scale", "nano-particle" or "nano-channel" relates to an average particle size or dimension of less than about 1000 nm, particularly less than about 200 nm, more particularly between about 1 nm to about 100 nm. As used herein, "micro", "micro-sized", "micro-scale", "micro-particle" or "micro-channel" relates to an average particle size or dimension of less than about 1000 um, particularly less than about 200 um, more particularly between about 1 um to about 100 um. In some instances, a dimension is provided herein in microns that is less than 1 um (e.g. 0.2 microns or 200 nm). Thus, "nano" and "micro" as used herein to refer to size are not necessarily mutually exclusive.

The devices and systems described herein can incorporate any of a variety of features described herein and the elements or features of one implementation of a device and system described herein can be incorporated alternatively or in combination with elements or features of another implementation of a device and system described herein as well as the various implants and features described in U.S. Pat. Nos. 8,399,006; 8,623,395; PCT Pat. Publication No. WO 2012/019136; PCT Pat. Publication No. WO 2012/019047; and PCT Pat. Publication No. WO 2012/065006. For example, the porous structures described herein may be used with any of the various implementations of a device or system. For the sake of brevity, explicit descriptions of each of those combinations may be omitted although the various combinations are to be considered herein. Additionally, described herein are different methods for implantation and access of the devices. The various implants can be implanted, filled, refilled etc. according to a variety of different methods and using a variety of different devices and systems. Provided are some representative descriptions of how the various devices may be implanted and accessed, however, for the sake of brevity explicit descriptions of each method with respect to each implant or system may be omitted.

The porous structures (also referred to herein as a release control element, RCE, frit, filter, membrane, or substrate) as described herein can be used with a number of various different implantable therapeutic devices including one or more of those devices described U.S. Pat. Nos. 8,399,006; 8,623,395; PCT Pat. Publication No. WO 2012/019136; PCT Pat. Publication No. WO 2012/019047; and PCT Pat. Publication No. WO 2012/065006; the entire disclosures of which are incorporated herein by reference thereto.

The porous structures described herein can be incorporated into an implantable therapeutic device that is positioned in a variety of locations in the body. The devices and systems described herein can be used to deliver therapeutic agent(s) for an extended period of time to one or more of the following tissues: intraocular, intravascular, intraarticular, intrathecal, pericardial, intraluminal, intraperitoneal, central nervous system, intraosseous, intramuscular, intradermal, intralesional, intrarterial, and others. The devices and systems described herein can be used to deliver one or more therapeutic agents locally or systemically.

Although specific reference may be made below to the delivery of treatments to a particular region of the body, such as the eye or another region, it also should be appreciated that delivery of treatments to other regions of the body to treat various medical conditions besides ocular conditions are considered herein. For example, conditions that may be treated and/or ameliorated using the drug delivery devices and methods described herein may include at least one of the following: hemophilia and other blood disorders, growth disorders, diabetes, leukemia, hepatitis, renal failure, HIV infection, Alzheimer's, hereditary diseases such as cerebrosidase deficiency and adenosine deaminase deficiency, hypertension, septic shock, autoimmune diseases such as multiple sclerosis, Grave's disease, systemic lupus erythematosus and rheumatoid arthritis, shock and wasting disorders, cystic fibrosis, lactose intolerance, Crohn's disease, inflammatory bowel disease, gastrointestinal or other cancers, degenerative diseases, trauma, multiple systemic conditions such as anemia, and ocular diseases such as, for example, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors such as neoplasms and retinoblastoma, angiogenesis, neoplasm, abnormal new cell growth, cancerous growths, tumors and the like. Any number of drug combinations can be delivered using any of the devices and systems described herein.

Figure 2:
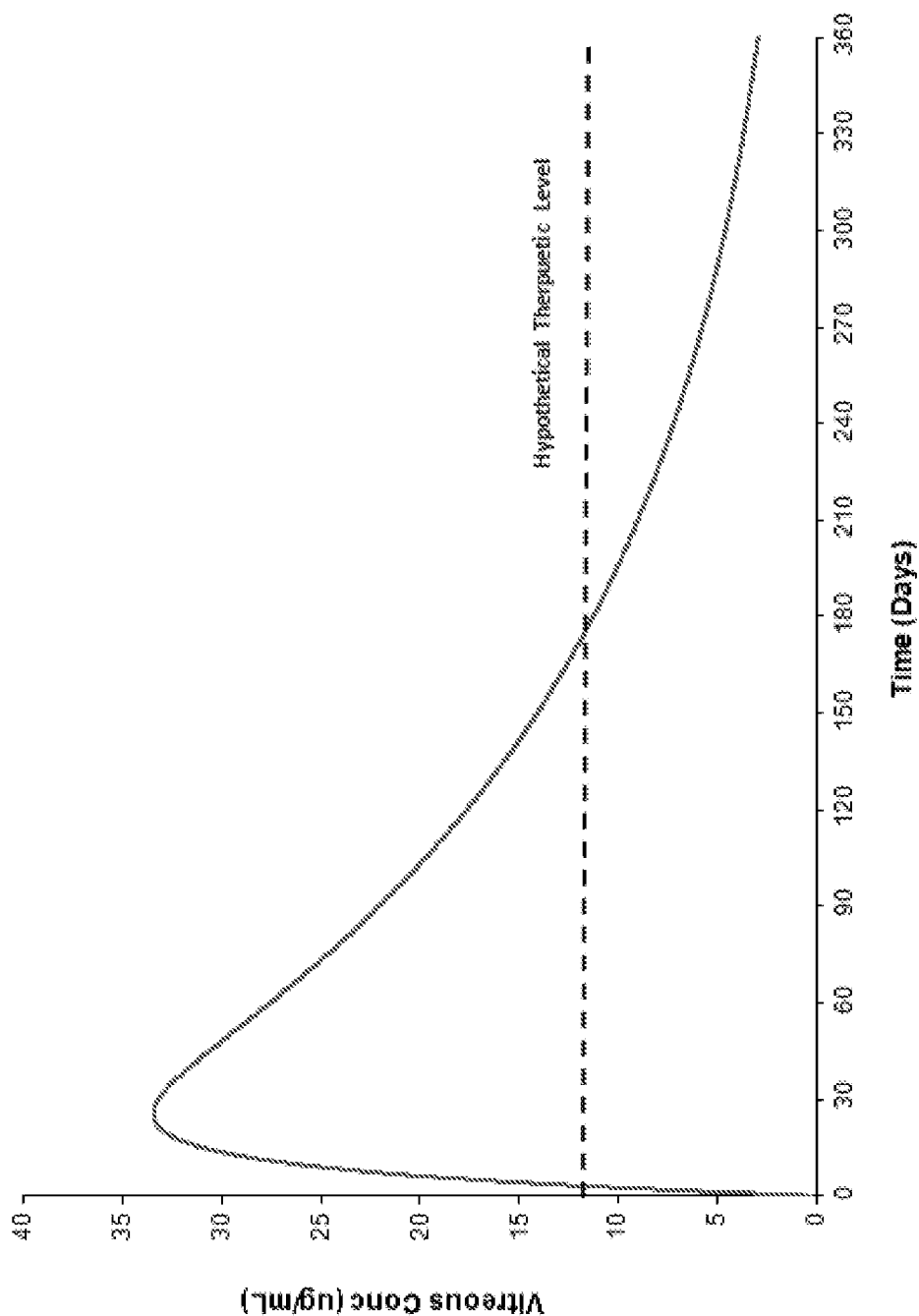
FIG. 2 illustrates a corresponding plot of drug concentration in a target body location.
Figure 3A:
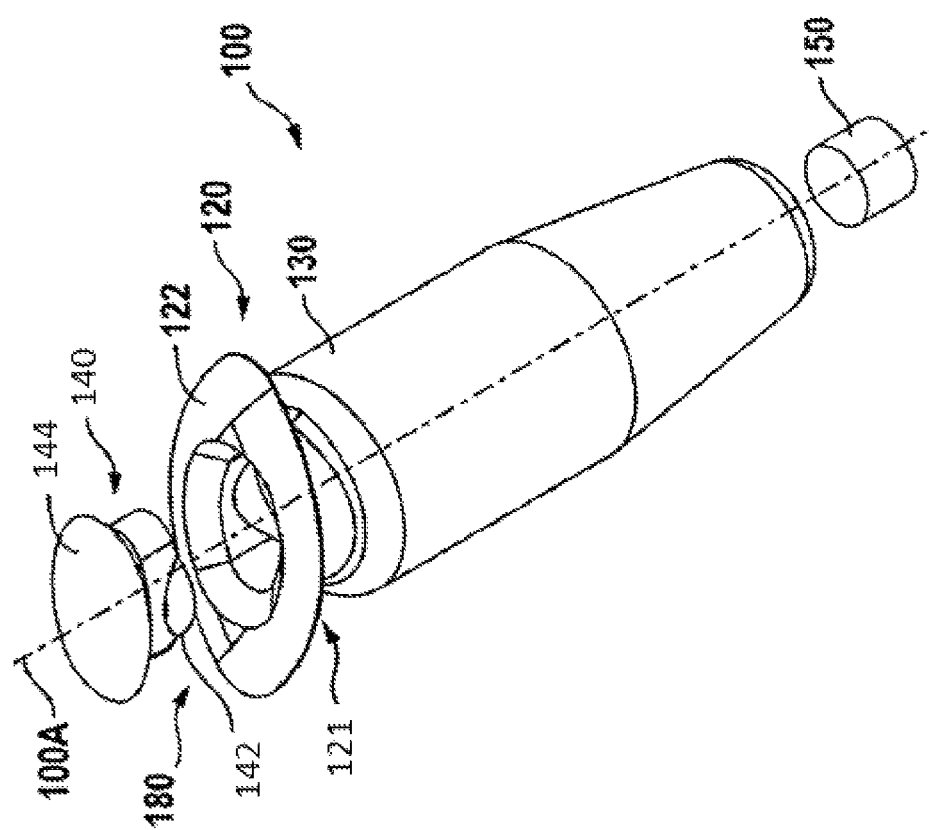
FIG. 3A is an exploded, perspective view of an implementation of a therapeutic device.
Figure 3C:
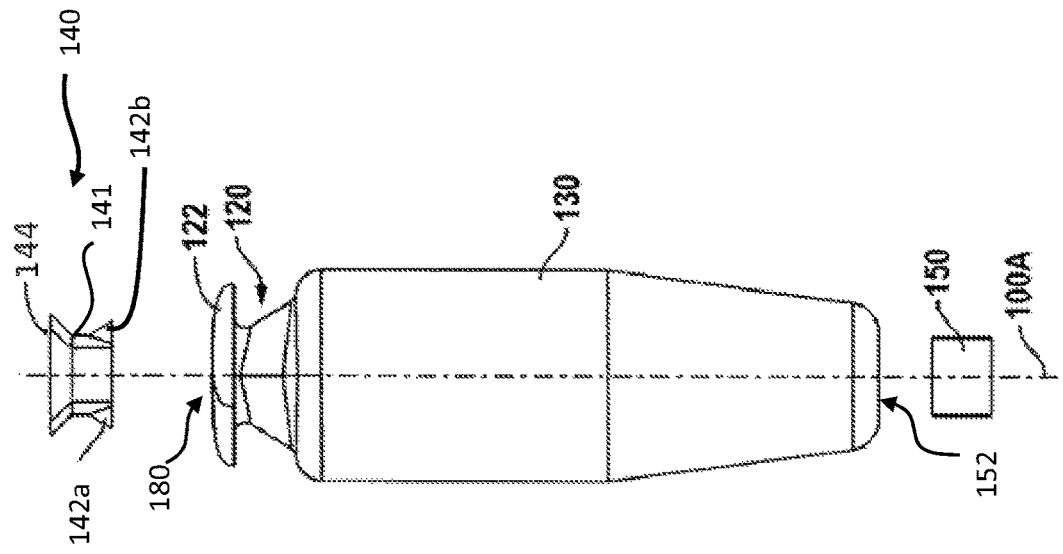
FIGS. 3B-3C are exploded, side views of the therapeutic device of FIG. 3A.
Figure 3B:
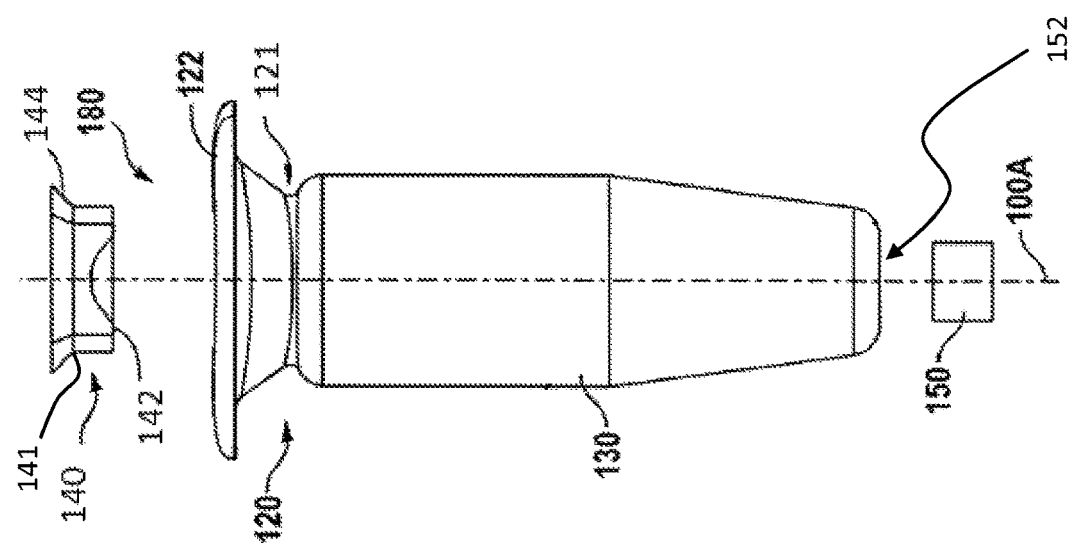
Figure 3D:
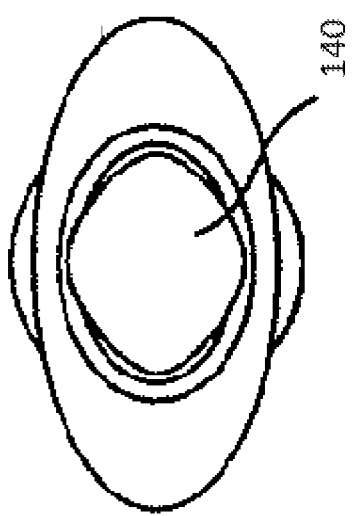
FIGS. 3D-3E are top and bottom views, respectively, of the therapeutic device of FIG. 3A.
Figure 3E:
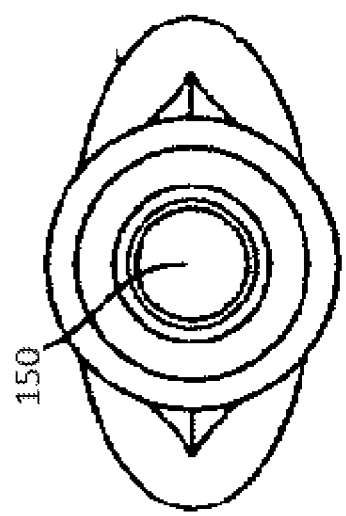
Figure 3F:
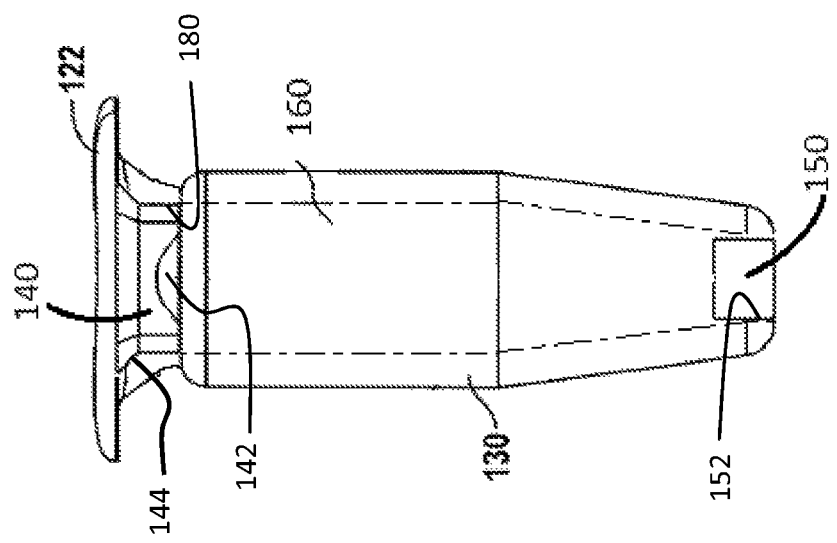
FIG. 3F is a side, cross-sectional view of the therapeutic device of FIG. 3A.

The release of a therapeutic agent from a therapeutic device can follow Fick's Law of Diffusion that yields a release rate decay that follows a first order profile. FIG. 1 illustrates a hypothetical example of a Fickian release profile and FIG. 2 illustrates a corresponding plot of drug concentration in a target body location (e.g. the vitreous of an eye). In general, the therapeutic device can maintain a therapeutic level of the drug in the target body location for an extended period of time. Often therapeutic devices have a first order release rate profile. However, in order to maintain the desired therapeutic levels even at the later time points, the device is "tuned" to release more than therapeutic levels at the earlier time points. Alternate mechanism(s) of release via diffusion may be effective in mitigating the early release of drug that is in excess of that needed for therapeutic benefit. For example, the rate of molecular diffusion can be inhibited by limiting the size of the pores through which drug molecules pass, otherwise known as "constrained diffusion." In constrained diffusion systems, a high concentration gradient can exist and be sustained. Such a system can be "tuned" to release at a more uniform, therapeutically targeted rate. Ideally, a therapeutic device has a "zero order" release rate rather than a first order release such that it releases consistently at a rate to maintain a target body concentration of drug this is slightly above the therapeutic level. Various materials can have a molecule-to-pore size ratio that may be suitable to yield a constrained diffusion release rate profile. Incorporation of such materials into a therapeutic device may be feasible, but can require explicit evaluation and iterative development for each molecule/clinical target of interest.

The implantable therapeutic devices considered herein can include a hollow, non-porous or nun-permeable housing having an inner surface defining, at least in part, a reservoir chamber for holding therapeutic material. The implantable therapeutic device can also include one or more porous structures for controlled sustained release of the therapeutic agent from the reservoir chamber via passive molecular diffusion driven by a concentration gradient across the porous structure.

FIGS. 3A-3F shows an implementation of an implantable therapeutic device 100 having a hollow housing 130, a reservoir chamber 160 for holding therapeutic material and one or more porous structures 150 for controlled sustained release of the therapeutic material from the reservoir chamber 160. It should be appreciated that the configuration of the therapeutic device 100 can vary and the device 100 shown is just one implementation. The housing 130 can have a proximal end region and a distal end region. The housing 130 can extend between the proximal end region and the distal end region along a longitudinal axis 100A such that the reservoir chamber 160 is symmetrically disposed about the axis. The reservoir chamber 160 can also be eccentrically disposed about the axis. The reservoir chamber 160 can be a fixed volume chamber or an expandable chamber. The reservoir chamber 160 can have a non-porous, non-permeable wall suitable for containing one or more therapeutic materials or agent(s) (see FIG. 3F). A penetrable barrier 140 can be positioned within a proximal end region of the housing 130 such as within an opening 180 in an access portion of the device that leads into a reservoir chamber 160 of the device. The porous structure 150 can be positioned within another region of the housing 130 a distance away from the penetrable barrier 140 such as within an opening 152 leading out of the reservoir chamber 160 of the device. For example, the porous structure 150 can be positioned near a distal end region of the housing 130 opposite the location of the more proximal penetrable barrier 140. It should also be appreciated that additional porous structures can be disposed along the Musing, for example the distal end of the housing can include a first porous structure, and one or more additional porous structures can be disposed along a portion of the housing proximal to the distal end, for example, along a tubular sidewall of the housing. The reservoir chamber 160 can have a volume sized to deliver therapeutic amounts of therapeutic agent to the eye for an extended period of time and the porous structure 150 can be configured to release therapeutic agent contained within the reservoir chamber 160 over the extended period of time, as will be described in more detail below.

The housing 130 can include a retention structure 120 that can protrude outward from the proximal end region of the housing 130. The access portion opening 180 can be an opening in the device 100 that extends into the reservoir chamber 160. The penetrable barrier 140 can be positioned, at least in part, within the access portion opening 180 such that it forms a seal with the proximal end region of the housing 130 and also allows access to refill or flush the device.

Again with respect to FIGS. 3A-3F and as mentioned above, a distal end region of the housing 130 can include another opening 152, for example, positioned near a distal end region of the housing 130 opposite the proximal access portion opening 180 into the reservoir chamber 160, that extends between the inside of the reservoir chamber 160 out of the housing 130. The porous structure 150 can be coupled to or positioned, at least in part, within the opening 152. The porous structure 150 can be affixed within opening 152 in distal end of housing 130, for example with glue or other material(s). Alternatively or in combination, the distal end of the housing 130 can include an inner diameter sized to receive the porous structure 150, and the housing 130 can include a stop to position the porous structure 150 at a predetermined location on the distal end so as to define a predetermined size of reservoir chamber 160. It should be appreciated that the porous structure 150 can be coupled to or positioned within other regions besides the distal end region of the housing 130. It should also be appreciated that more than one porous structure 150 can be coupled to, positioned within, or disposed along the housing 130. For example, the distal end of the housing 130 can include a first porous structure, and one or more additional porous structures can be disposed along a portion of the housing proximal to the distal end, for example, along a tubular sidewall of the housing. The one or more additional porous structures can be disposed in series such that the therapeutic device 100 has a first porous structure 150 acting as a release control element metering the diffusion of the therapeutic agent from the reservoir chamber and a second porous structure providing a barrier function, for example, by retaining immune cells, bacterial cells, and other undesired material within the reservoir and limiting or preventing such contaminants from exiting the reservoir and entering the eye. Additionally or alternatively, the second porous structure can provide a barrier function limiting or preventing contaminants from entering the device from inside the eye. A first type of porous structure can be positioned in series with another type of porous structure. For example, a sintered release control element having a particular thickness, porosity, and tortuosity can be positioned adjacent a filter membrane having a different thickness, porosity, and/or tortuosity. A first type of porous structure can be positioned in a distal opening of the reservoir chamber and a filter can be bonded on an inner surface of the porous structure, an outer surface of the porous structure or both an inner and an outer surface of the porous structure.

Still with respect to FIGS. 3A-3F, therapeutic formulations injected into device 100 can be released from the reservoir chamber 160 in accordance with the volume of the reservoir chamber 160 and a release characteristic or release rate index of the porous structure 150, which is described in more detail herein. The volume of the reservoir chamber 160 can be sized to deliver therapeutic amounts of a therapeutic agent to the patient for an extended period of time. The volume of the reservoir chamber 160 can be substantially determined by an inner cross sectional area of the housing 130, such as the distance between the proximal, penetrable barrier 140 and the porous structure 150.

One or more regions of the housing 130 of the devices described herein can be formed of a substantially rigid, biocompatible material. In some implementations, the walls of the housing 130 including at least the proximal retention structure 120 down to and including the porous structure 150 are substantially rigid such that the reservoir chamber 160 has a substantially constant volume when the therapeutic agent is released from the device so as to maintain a stable release rate profile, for example when the patient moves. The reservoir chamber 160 can remain substantially rigid and have a substantially constant volume even during injection of the therapeutic agent into the device, for example a device already implanted in the patient. It should be appreciated that the therapeutic devices described herein can incorporate an expandable reservoir chamber 160 such as described in U.S. Publication No. 2016/0128867, which is incorporated herein by reference.

One or more regions of the housing 130, one or more regions of the retention structure 120 as well as other portions of the devices described herein, alone or in combination, can be formed of one or more of many biocompatible materials including, but not limited to materials such as acrylates, polymethylmethacrylate, siloxanes, metals, titanium stainless steel, polycarbonate, polyetheretherketone (PEEK), polyethylene, polyethylene terephthalate (PET), polyimide, polyamide-imide, polypropylene, polysulfone, polyurethane, polyvinylidene fluoride, polyphenylene polyphenylsulfone or PTFE, and others. The material can also include biocompatible, optically transmissive materials such as one or more of acrylate, polyacrylate, methlymethacraylate, polymethlymethacrylate (PMMA), polycarbonate, glass or siloxane.

The reservoir chamber 160 can be filled and re-filled as needed, such as after implantation of the device in the patient. As mentioned above, the penetrable barrier 140 can be positioned, at least in part, within an access portion opening 180 sealing the reservoir chamber 160 on a proximal end region of the device 100. The penetrable barrier 140 can be a septum configured to receive and be repeatedly penetrated by a sharp object such as a needle for injection of the therapeutic agent into the reservoir chamber 160. The penetrable barrier 140 can be configured to re-seal when the sharp object is removed. The penetrable barrier 140 can be a pre-molded soft, high strength material. In some implementations, the penetrable barrier 140 can be formed from one or more elastic materials such as siloxane, rubber, or another liquid injection molding silicone elastomer such as NUSIL MED-4810, NUSIL MED-4013, and others (NuSil Silicone Technology, Carpinteria, CA). In some implementations, the penetrablebarrier 140 can include an opaque material and/or a colored material such that it can be visualized by the treating physician. In other implementations, the penetrable barrier can be a translucent material such that the penetrable barrier appears dark when the therapeutic device is implanted in the eye and viewed from outside the eye by a treating physician. The dark region forms a penetration target for refilling of the device when the device is still implanted in tho eye.

As mentioned above, the implantable therapeutic device 100 can include a porous structure 150 for controlled release of the therapeutic agents from the reservoir chamber 160. The porous structure 150 can allow for controlled release of the therapeutic agent via passive molecular diffusion driven by a concentration gradient across the porous structure 150. Porous structures considered herein are described in U.S. Pat. Nos. 8,399,006; 8,623,395; PCT Publication No. WO 2012/019136; PCT Publication No. WO 2012/019047; and PCT Publication No. WO 2012/065006; the entire disclosures of which are incorporated herein by reference thereto.

FIGS. 3A-3C, 3F, and 4A-4D show implementations of a porous structure 150 configured to release the therapeutic material from the reservoir chamber 160. The porous structure 150 can be configured in many ways to release the therapeutic agent in accordance with an intended release profile. The porous structure 150 may include one or more of a permeable membrane, a semi-permeable membrane, a material having at least one hole disposed therein, nano-channels, nano-channels etched in a rigid material, laser etched nano-channels, a capillary channel, a plurality of capillary channels, one or more tortuous channels, tortuous microchannels, sintered nano-particles, an open cell foam or a hydrogel such as an open cell hydrogel. The porous structure 150 can be the release control element configured to meter drug delivery to the patient.

In some implementations, the porous structure 150 can be composed of interconnected particles or grains of material. Minute spaces or void space can extend throughout the porous structure 150 between the sintered material. The void space within the sintered material can contribute to the porosity of the porous structure 150. Without limiting this disclosure to any particular theory or mode of operation, the porous structure 150 can be designed to have a pore size that retains or inhibits passage of molecules, cells, or solid particles of a certain size range and allows for passage of molecules, cells, or solid particles of another size range through the porous structure 150. The porous structures may be described herein as having an average pore size or void space dimension to define the porous structure utility for allowing a molecule to substantially pass through a porous structure or to substantially limit a molecule from passing through the porous structure. As such, the molecules of a particular size range (e.g. therapeutic agent) can passively diffuse from within the reservoir chamber 160 within the porous structure outward along a concentration gradient from one side of the porous structure 150 to another side of the porous structure 150 such that therapeutic quantities of the therapeutic agent are delivered for the extended time.

The material forming the porous structure 150 can include sintered material including at least one of a metal, a ceramic, a glass or a plastic. The sintered material can include a sintered composite material, and the composite material can include two or more of the metal, the ceramic, the glass or the plastic. The metal can include at least one of Ni, Ti, nitinol, stainless steel including alloys such as 304, 304L, 316 or 316L, cobalt chrome, elgiloy, hasteallody, c-276 alloy or Nickel 200 alloy. The plastic can include a wettable coating to inhibit bubble formation in the channels, and the plastic can include at least one of polyether ether ketone (PEEK), polyethylene, polypropylene, polyimide, polystyrene, polycarbonate, polyacrylate, polymethacrylate, or polyamide.

In some implementations, the porous structure 150 is formed from an all-metal filter media. The all-metal filter media can be metal fiber or metal powder based media. In some implementations, the powder or grains of material used to form the porous structure 150 can have an average size of no more than about 20 um, or no more than about 10 um, an average size of no more than about 5 um, or an average size of no more than about 1 um, or an average size of no more than about 0.5 um. The all-metal filter media can be sintered porous metal media (Mott Corporation. Farmington, Conn.) The filter media can have a grade that can substantially stop solid particles having a nominal solid particle size from penetrating the media. In some implementations, the sintered material includes grains of material corresponding to a Media Grade of no more than about 0.1, or no more than about 0.2, or no more than about 0.3, or no more than about 0.5 (Media Grade as determined by ISO 4003 or ASTM E128). In some implementations, the starting raw material for the porous structure 150 can be metal powder particles sintered together. The particle size distribution of the starting raw material can be between about 50 nm and about 350 nm or between about 50 nm to about 50 um, as well as any number microns in between depending on the powder particle size distribution desired. In other implementations, the particle size distribution of the starting raw material can be no more than about 20 um, no more than about 10 um, no more than about 5 um, no more than about 1 um, or nor more than about 0.5 um, or no more than about 0.3 um, or no more than about 0.2 um.

In some implementations, the sintered material allows passage during filtration solid particles having a size of about 0.1 microns or less, about 0.2 microns or less, about 0.3 microns or less, and about 0.5 microns or less. In some implementations, the porous structure 150 has pores having a diameter or pore size of approximately 0.2 um, 0.3 um, 0.4 um, 0.5 um, 1 um, 2 um, 3 um, 4 um, or 5 um. In some implementations, the porous structure 150 has an average pore size of about 5 um up to about 50 um. In some implementations, the porous structure 150 allows for passage of particles smaller than a size ranging between 0.1 um-100 um and largely blocks passage of particles having a size greater than this size range. The pores of the porous structure 150 can be substantially larger than the molecules of interest that are to diffuse through the porous structure 150. For example, the pores of the porous structure 150 can be 2, 5, 10, 15, 20, 25, 30, 35, 40, 45, 50, 75, or 100 times larger than the molecules of interest to diffuse through the porous structure 150. In some implementations, therapeutic compounds in the size range of IgG (150 kDa or 10.5 nm hydrodynamic diameter) or BSA (69 kDa or 7.2 nm hydrodynamic diameter) can diffuse relatively easily through the void space of the porous structure 150. The pore size can be representative of the dimension of the void space extending throughout the porous structure 150. However, It should be appreciated that some regions within the void space can neck down to a smaller size than a neighboring pore or can widen into a larger size than a neighboring pore. Generally as used herein, average pore size refers to a dimension of the porous structure 150 that provides information as to whether or not a particle of a particular size range can largely pass through the porous structure 150 or be largely captured, retained, blocked, and/or rejected by the porous structure 150.

The porous structure 150 can have a fixed tortuous, porous material such as a sintered metal, a sintered glass, or a sintered polymer with a defined porosity and tortuosity that controls the rate of delivery of the at least one therapeutic agent to the target body. The void space within the porous structure 150 can be characterized as having a plurality of channels (e.g. micro-channels and/or nano-channels) extending between pores or openings in the first side and pores or openings in the second side. The diameter of the channels may have a dimension across that allows for, impairs or prevents movement of molecules having a particular size through them. In some implementations, the diameter of the channels are about 10 nm across to about 1000 nm across, or larger. The channels can be substantially straight or can be tortuous. The porosity or percentage of void space throughout the porous structure 150 can be within a range from about 3% to about 70%. In other embodiments, the porosity or percentage of void space is within a range from about 5% to about 10% or from about 10% to about 25%, or, for example, from about 15% to about 20%. Porosity can be determined from the weight and macroscopic volume or can be measured via nitrogen gas adsorption.

Microbes including bacteria and/or fungal spores as well as immune cells and cellular products such as antibodies can be inhibited from filtering through the void space within the sintered material of the porous structure 150. For example, the pore size or dimension of the channels through the porous structure can be of a particular small size range to retain such material. In some implementations, pore sizes for the porous structure 150 are, for example, between 3 and 5 microns, or 3 and 10 microns, up to about 50 microns. However, pore sizes in this range can allow certain microbes to pass through the porous structure 150. If a microbe is inadvertently introduced into the reservoir chamber 160 of the implantable device 100, the microbe can eventually pass through the device into the surrounding tissue region of the patient. In addition, if bacteria exists in the eye of the patient from another source unrelated to the implant, it may filter into the implant during diffusion. Thus, pore sizes of a certain range pose a risk of infection to the patient. Microbes as well as immune cells such as macrophages, cellular products, or other molecules from the patient, bacteria can pass into the reservoir chamber 160 through the porous structure 150 having pore sizes of a certain range. Porous structures having a pore size that is approximately 0.2 microns or smaller generally inhibit microbial and immune cell infiltration. However, a porous structure 150 having a pore size in this range can inhibit target release rate of the therapeutic agent from the reservoir. Further, implantable therapeutic devices having porous structures can release an amount of drug through the porous structure during in situ filling or refilling due to a transient increase in pressure inside the device associated with resistance of fluid being forced through the refill needle system. In the case of a therapeutic device that is already implanted in a patient prior to filling, this bolus release of drug during filling can be undesirable. It can be useful to control whether and how much of a bolus is released during filling.

As will be described in more detail below, the therapeutic devices described herein can incorporate a porous barrier layer 155 that allows the therapeutic agent of interest to pass through, but inhibits microbial and cellular infiltration. As will be described in more detail below, the porous barrier layer 155 can also mitigate bolus release during refilling of the reservoir by providing a dense pressure barrier. Mitigating bolus release can be useful, for example, during flushing of a device exhibiting signs of contamination. The reservoir chamber of the device can be flushed with an anti-bacterial agent (or other type of agent) prior to refilling the device with a therapeutic for treating of the eye disease without fear of pushing the contamination into the eye.

The porous structures 150 can be covered on at least a first surface by the porous barrier layer 155. The porous barrier layer 155 can be a coating over a distal end region of the device or on one or more surfaces of the porous structure 150. The barrier layer 155 can also be a discrete porous structure positioned in series with the porous structure 150. The barrier layer 155 can be bonded on, positioned internal to or formed on an inner-facing surface of the porous structure 150 (i.e. a surface that faces internal to the reservoir of the device) or an outer-facing surface (i.e. a surface that faces external to the reservoir of the device), or both an inner and an outer facing surface when the porous structure 150 is assembled with the therapeutic device 100 within the opening 152.

The porous structure 150 can be configured to control the diffusion rate of the therapeutic agent from the reservoir chamber 160 and the barrier layer 155 can inhibit passage of certain contaminants (e.g. microbes, bacteria, cellular material, cell types, macrophages, cellular products, fungal spores, etc.) from exiting and/or entering the reservoir chamber 160 through the porous structure 150. Release rate is described in more detail below, but generally is a function of the concentrations of the therapeutic on either side of the porous structure (i.e. inside the reservoir and outside the reservoir), the diffusion coefficient of the therapeutic in the solution, porosity of the porous structure, tortuosity of the channels or void spaces in the porous structure, area of the porous structure, and thickness of the porous structure. The barrier layer 155 can inhibit penetration of contaminants without substantially impacting the metered diffusion rate of the drug that would otherwise be achieved by the porous structure 150 in absence of the barrier layer 155. Alternatively, the porous structure 150 and/or the barrier layer 155 can be selected based on certain characteristics (e.g. porosity, thickness, tortuosity, area) such that the desired diffusion rate or release rate of the therapeutic agent from the reservoir chamber 160 is achieved even in spite of the barrier layer 155.

The porous structure 150 acts as the release control element providing predictable metering of the drug diffusion into the eye whereas the barrier layer 155 limits or prevents contaminants from passing through the porous structure 150 along with the drug. The barrier layer 155 can have a substantially different porosity compared to the porosity of the porous structure 150 alone. As described above, the porous structure 150 can have minute spaces or void space forming channel structures disposed between pores in a first surface and pores in a second surface of the porous structure 150. The channel structures can be within the micro-channel and/or nano-channel size range. The porous structure 150 can have a first pore size or void space dimension that allows for molecules having a first size to pass through the porous structure 150, such as the therapeutic agent as well as molecules significantly larger than the therapeutic agent such as bacteria. The barrier layer 155 can have a pore size or void space dimension that is smaller than the pore size or void space dimension of the porous structure 150. The pore size or void space dimension of the barrier layer 155 is large enough to allow the therapeutic agent to penetrate the barrier layer 155, but limits or prevents larger sized molecules such as bacteria or immune cells or other contaminants from being able to penetrate the barrier layer 155. Thus, the pore size or void space dimension of the barrier layer 155 can retain a larger range of molecules including those that are sized smaller than would otherwise be retained by the porous structure 150 alone. The barrier layer 155 on or adjacent the first and/or second surface of the porous structure 150 can effectively reduce the size of the molecule that can enter the porous structure 150 without impacting the channel dimension such that the permeability of a drug molecule through the void space of the porous structure 150 is maintained substantially the same.

The barrier layer 155 is adapted to reject or substantially block passage of particles having an average particle size within an average particle size range that is greater than about 1 nm-10 nm, or greater than about 0.01 um—0.1 um, or greater than about 0.1 um-1 um such that the barrier layer 155 rejects or blocks passage of particles having an average particle size within an average particle size range that is greater than about 0.001 um to about 1 um. In some implementations, the porous structure 150 allows passage of particles having a size range up to about 3 um or up to about 50 um whereas the barrier layer 155 rejects or blocks passage of particles having an average particle size greater than about 0.1 um to about 1 um. As such, the barrier layer 155 rejects or blocks passage of particles having a size that would otherwise be allowed to pass through the porous structure 150. For example, the barrier layer 155 may reject or block passage of particles having an average particle size greater than about 0.1 um up to greater than about 3 um, or particles having an average particle size greater than about 0.1 um up to greater than about 4 um, or particles having an average particle size greater than about 0.1 um up to greater than about 5 um.

As mentioned, the barrier layer 155 can be a discrete porous structure positioned in series with another porous structure. Each porous structure 150 can be configured to release the therapeutic agent for an extended period while having certain diffusion characteristics. The one or more porous structures 150 coupled together in series can be coupled together in any of a number of configurations. For example, a first porous structure 150 can be positioned within an interior of the reservoir chamber 160 proximal to the opening 152 leading out of the reservoir chamber 160 and a second porous structure can be positioned within the opening 152. Alternatively, a first porous structure 150 can be positioned within the opening 152 and a second porous structure can be positioned at a distal end of the first porous structure 150 outside the reservoir chamber 160. In either version, the two porous structures positioned in series can be in direct contact with one another or can be separated a distance away from one another. The porous structures positioned in series can be two or more porous structures formed of the same material or different materials. The porous structures positioned in series generally have different porosity in that a first porous structure retains molecules having a size range that would not be retained by the second porous structure. For example, the first porous structure may have a porosity that allows for bacterial cells to penetrate therethrough and the second porous structure may have a porosity that limits or substantially prevents molecules in this size range from penetrating therethrough. Each of the first and second porous structures, however, would allow for the therapeutic agent to be delivered to the patient to penetrate at a predictable diffusion rate. In some implementations, the first porous structure 150 can be a sintered release control element and the barrier layer 155 can be a separate filter membrane formed of a different material. The release control element may have certain defined parameters such as thickness, area, porosity, tortuosity and allow for drug delivery according to a particular release rate index as described elsewhere herein. The filter membrane may have defined parameters that are different from the release control element such that the filter membrane acts as a barrier to certain molecules, but has minimal impact on the release rate index of the release control element. For example, the filter membrane may have a significantly smaller thickness compared to the release control element. The filter membrane may have smaller porosity and/or tortuosity. Regardless, the combination of the release control element and the filter membrane may maintain the particular release rate index as if the filter membrane were not present.

Figure 7B:
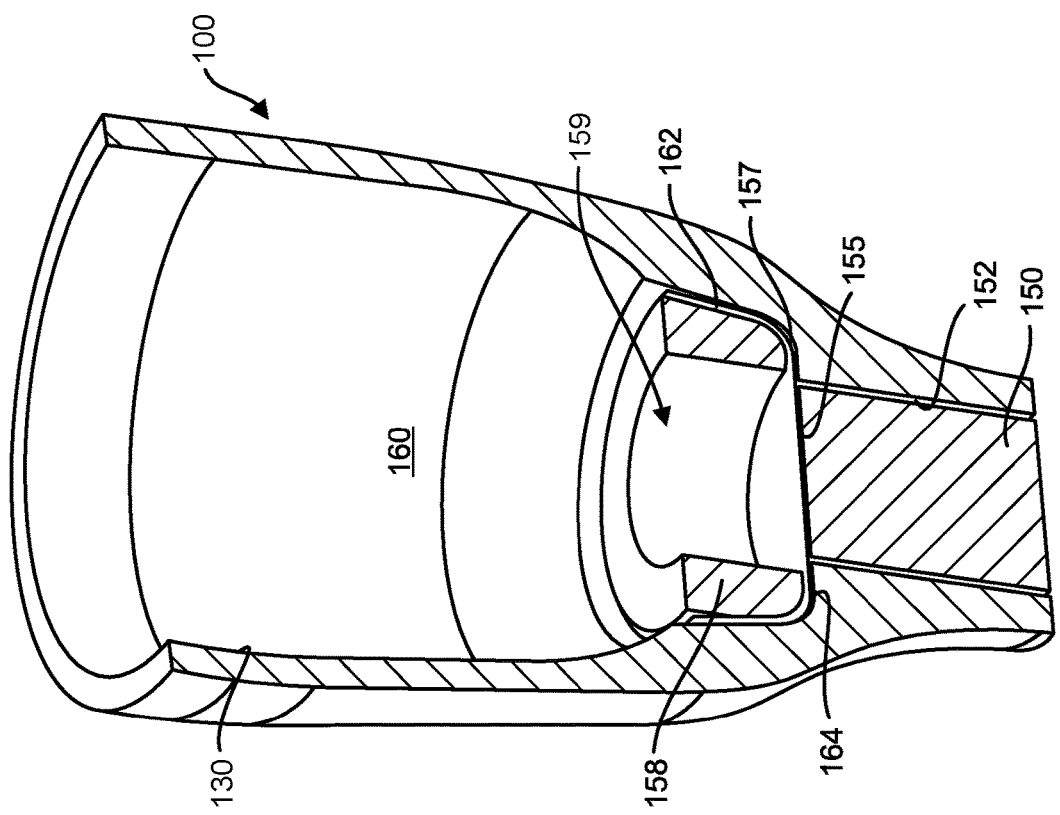
FIGS. 7B-7D are partial, cross-sectional views of distal end regions of therapeutic devices having porous structures in series.
Figure 7A:
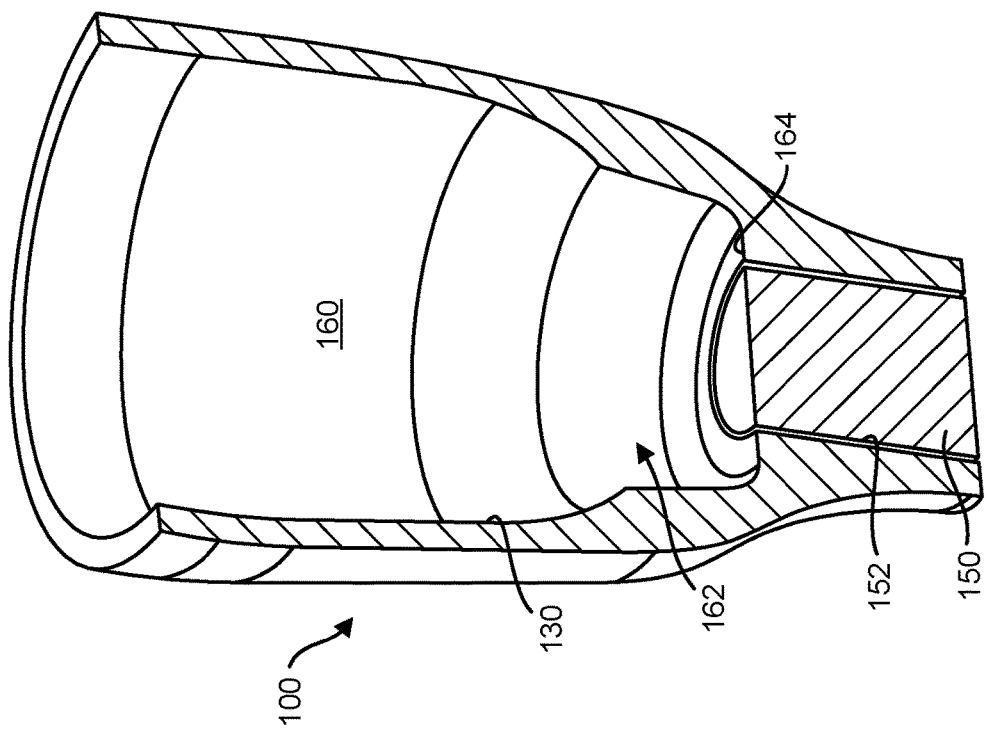
FIG. 7A is a partial, cross-sectional view of a distal end region of a therapeutic device.

FIG. 7A shows a distal end of an implementation of a therapeutic device 100. The device 100 has a hollow housing 130 with walls formed of a non-permeable material and defining a reservoir chamber 160 for holding therapeutic material. A first porous structure 150 for sustained release of the therapeutic material from the reservoir chamber 160 is positioned within an opening 152 leading out of the reservoir chamber 160. FIG. 7B shows the distal end of the therapeutic device of FIG. 7A and having a barrier layer 155 formed by a discrete porous structure coupled within the reservoir chamber 160 in series with the first porous structure 150. The barrier layer 155 in this implementation can be a filter membrane separate from the first porous structure 150.

Figure 7C:
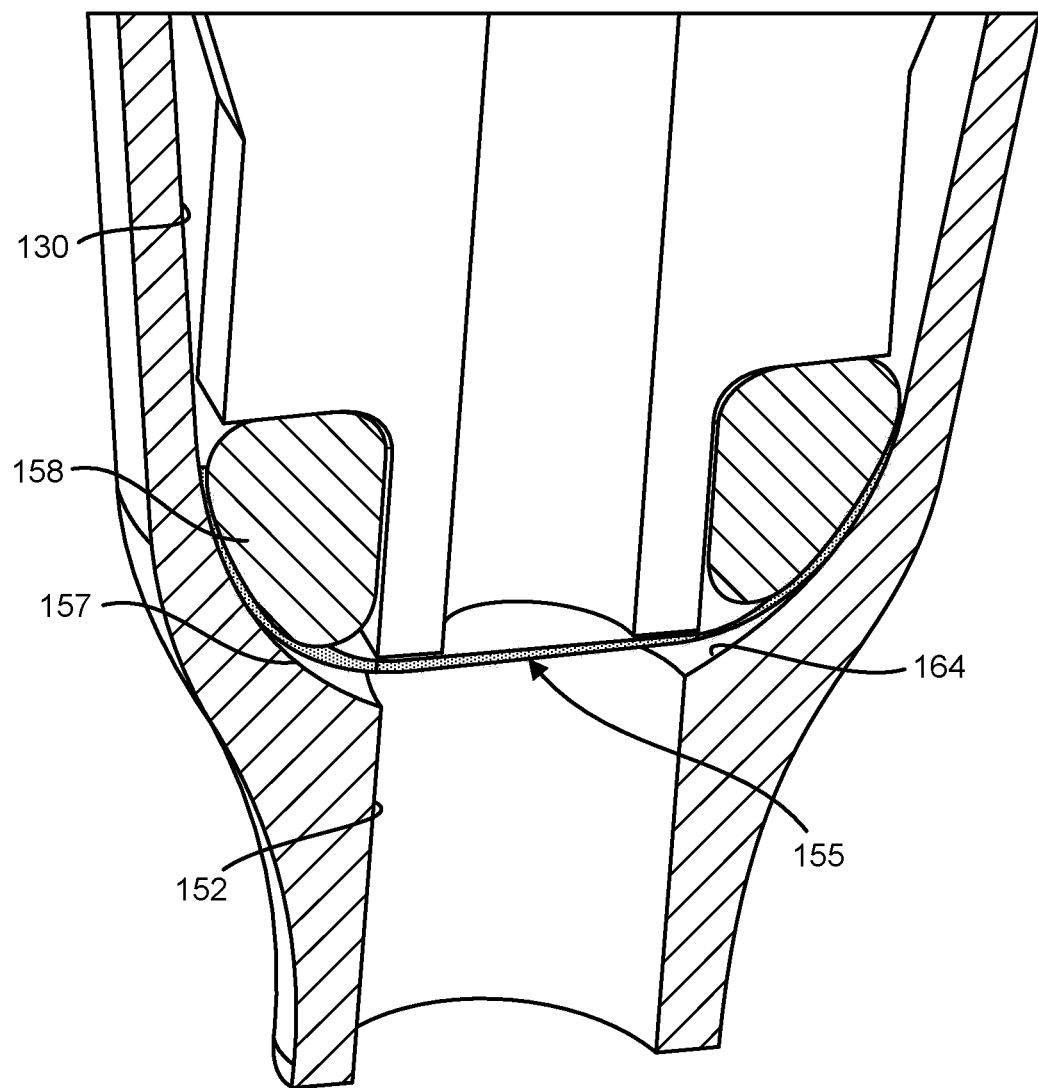

Still with respect to FIG. 7B, the chamber 160 can taper down towards the opening 152 such that a region 162 at a distal end of the reservoir chamber 160 is formed having a narrower diameter than a more proximal region of the reservoir chamber 160. A distal ledge 164 can surround the opening 152 within with the porous structure 150 is positioned. The barrier layer 155 can be positioned within the region 162 between the porous structure 150 positioned within the opening 152 and the distal end region of the reservoir chamber 160. The distal ledge 164 surrounding the opening 152 can be sized to receive a perimeter edge 157 of the barrier layer 155 such that a central region of the barrier layer 155 aligns with the opening 152 and thus, the porous structure 150 positioned within the opening 152. The barrier layer 155 can be fixed in place by a bushing 158 or capture ring. The bushing 158 can be positioned over the perimeter edge 157 of the barrier layer 155 capturing the barrier layer 155 against the distal ledge 164. The bushing 158 can be an annular element formed of PMMA. The inner aperture 159 of the bushing 158 allows for communication between the reservoir chamber 160 and the barrier layer 155. The outer surface of the bushing 158 can be shaped to conform to the inner wall 130 of the reservoir chamber 160 within which it is positioned. The outer surface of the bushing 158 can be generally cylindrical to fit within region 162 at the distal end of the reservoir chamber 160. FIG. 7C shows another implementation of the therapeutic device 100 having a barrier layer 155 captured by a bushing 158. In this implementation, the barrier layer 155 is positioned within the distal end of the reservoir chamber 160 and the outer surface of the annular bushing 158 captures the perimeter edge 157 of the barrier layer 155 against the wall 130 of the reservoir chamber 160 as well as the distal ledge 164 formed around the opening 152. Thus, the diameter of the barrier layer 155 in this implementation can be larger than the inner diameter of the distal end of the reservoir chamber 160. The outer surface of the bushing 158 can be shaped to conform to the inner wall 130 of the reservoir chamber 160 such that the bushing 158 can engage and be press-fit into the reservoir chamber 160 to capture the perimeter edge 157 of the barrier layer 155.

Figure 7D:
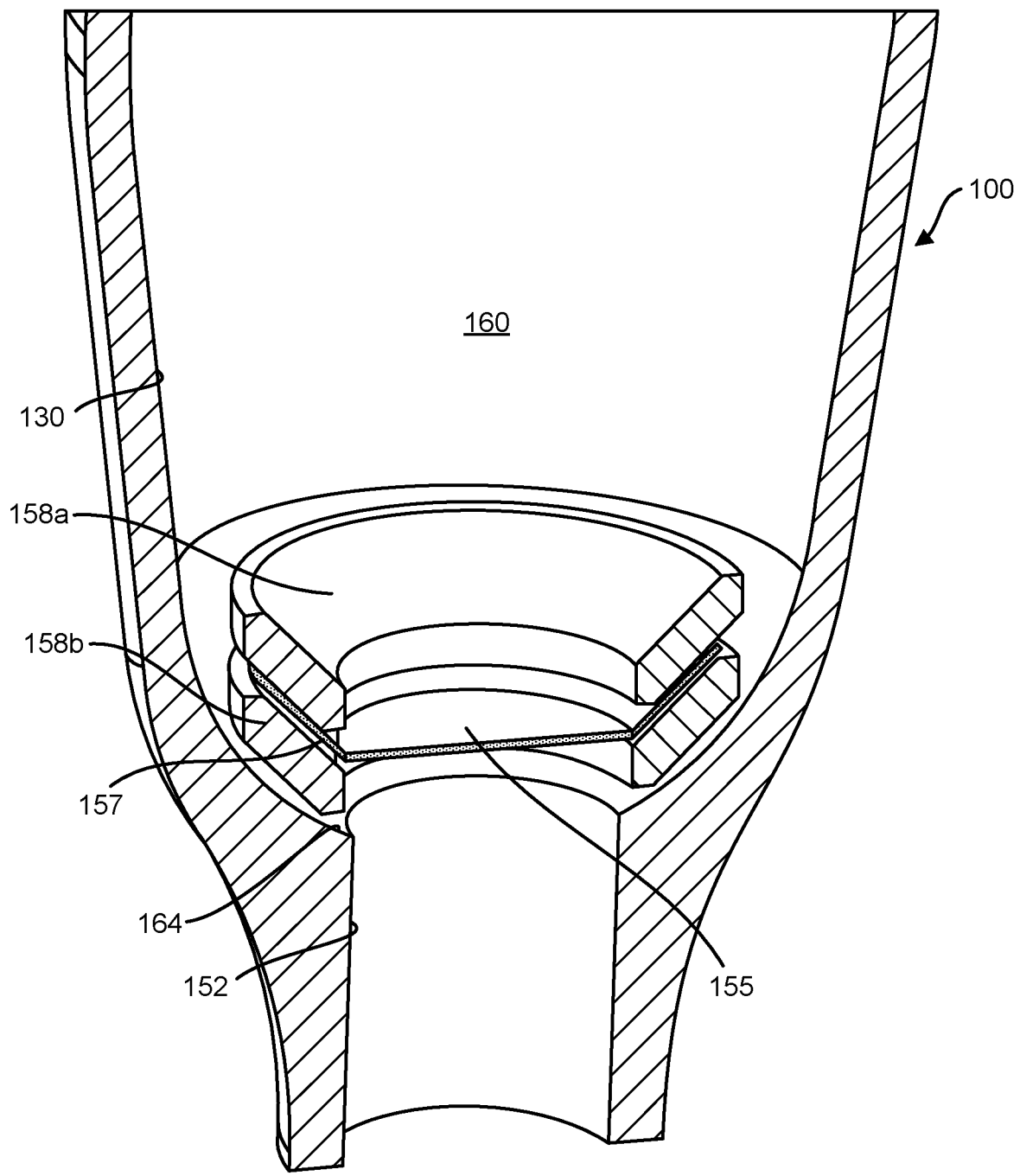

FIG. 7D illustrates a distal end region of a reservoir chamber 160 of a therapeutic device 100 having a double bushing 158. The perimeter edge 157 of the barrier layer 155 can be captured between two bushings 158a, 158b. As with other implementations, a distal ledge 164 can be formed around the opening 152 from the reservoir chamber 160. The double bushing can include a first bushing 158b positioned against the distal ledge 164 and a second bushing 158a positioned towards the reservoir chamber 160. The perimeter edge 157 of the barrier layer 155 can be captured between the first bushing 158b and the second bushing 158b such that the central region of the barrier layer 155 is positioned over the opening 152. Each of the first and second bushings 158a, 158b can be annular or ring-shaped such that they can capture the perimeter edge 157 between them while maintaining the central region of the barrier layer 155 to freely communicate with the reservoir chamber 160. The annulus can have any of a variety of shapes. Each of the double bushings can have a generally cylindrical annulus like the bushing 158 shown in FIG. 7B. The double bushings can be toroid-shaped or otherwise rounded such as the bushing 158 shown in FIG. 7C. The annulus of each of the double bushings can also have a frusto-conical shape, a tunnel shape, toroid, flattened toroid, or a bowl shape. The perimeter region 157 can be captured between flattened sides of the annulus and the central region of the barrier layer 155 can align with the central aperture of the bushing 158. The double bushing 158 can be pre-fused and bonded in place with an adhesive or solvent.

It should be appreciated that the barrier layer 155 can be positioned relative to the porous structure 150 such that it is positioned on the reservoir side of the porous structure 150 or on the external side of the reservoir and porous structure 150. The barrier layer 155 can be positioned in contact with the porous structure 150 such as shown in FIG. 7B or the barrier layer 155 can be spaced apart from the porous structure 150 such as shown in FIG. 7D. It should also be appreciated that the barrier layer 155 can be coupled to the device using any of a number of techniques. The barrier layer 155 can be heat-fused, ultrasonically bonded, or adhered. Further, the barrier layer 155 can be formed of any of a variety of materials including porous metal as described elsewhere herein. In some implementations, the barrier layer 155 can be a membrane disc filter formed of silver metal, cellulose acetate, ceramic, glass fiber, borosilicate fiber, MCE (mixed cellulose ester), nylon, polyacrylonitrile (PAN), polycarbonate track etch (PCTE), polyethersulfone (PES), polyester track etch (PETE), polypropylene (PP), PTFE, PVDF, or other filter material such as those provided by Sterlitech Corp. (Kent, Wash.).

The barrier layer 155, whether it is a discrete porous structure such as the filter membranes described above or a coating on the porous structure, can contain contaminants introduced into the system from exiting into the eye and/or limit or substantially prevent contaminants from entering the system from the eye. Contaminants may be introduced into the system when the reservoir chamber is initially filled with therapeutic agent or refilled while the therapeutic device is still implanted in the eye. The barrier layer 155 can limit or prevent the release of these contaminants from the reservoir chamber 160 into the eye thereby reducing the risk of eye infections at least until the contamination is identified and the therapeutic device can be removed from the eye. In some implementations, the barrier layer 155 can limit or prevent the passage of contaminants from the reservoir into the eye for at least about 1 week, 1 month, or indefinitely. Contaminants can cause a change in the appearance of the contents in the reservoir chamber (e.g. cloudy) or result in irritation to the patient. The therapeutic device can be visually inspected by a physician following implantation such as by indirect ophthalmoscope or on a slit lamp.

In addition to limiting reservoir contamination and reducing the risk of an eye infection by containing contaminants within the system and limiting the release into the eye, the barrier layer 155 allows for flushing of the reservoir chamber without the need to remove the device from the eye. As described elsewhere herein, the barrier layer 155 can mitigate bolus release through the porous structure 150 during injections of fluid into the reservoir. Contamination of the reservoir chamber can be treated by flushing the system or injecting the system with antibiotics. Because bolus release is mitigated, the flushing and/or injection can be performed while the device is still implanted in the eye without fear of the contaminants being urged from the reservoir chamber through the porous structure into the eye. For example, a refill needle system such as that described in U.S. Pat. No. 9,033,911 filed Aug. 5, 2011, or U.S. Publication No. 2013-0165860, filed Sep. 13, 2012, can be used to flush the system with saline followed by refilling the device with an antibiotic to eliminate the contaminant from the system. Once the system is treated for the contamination, the system can be further flushed with saline and the original therapeutic drug can be refilled into the system so the patient can continue treatment.

In some implementations, the porous structure 150 can have an average pore size that is between about 0.2 um to about 5 um and a porosity that is between about 10% to about 30%. The barrier layer 155 can have an average pore size that is approximately 0.2 microns or less, approaching the size of the therapeutic being delivered. As such, the barrier layer 155 retains molecule that are smaller than would otherwise be retained by the porous structure 150. Or said another way, certain sized molecules retained or blocked by the barrier layer 155 would not be retained or blocked by the porous structure 150. The porosity P of the barrier layer 155 can be substantially less than the porosity of the porous structure 150 alone. The substantially reduced porosity of the barrier layer 155 can result in an overall denser material as compared to the porous structure 150. In some implementations, the porosity of the barrier layer 155 can be between about 1% to about 15%. Despite the smaller pore size and lower porosity of the barrier layer 155 compared to the porous structure 150 relative to which it is applied or used in conjunction with, in some implementations the release rate through the porous structure 150 and the barrier layer 155 can be maintained or comparable to the release rate through the porous structure 150 alone as if the barrier layer 155 were not present. For example, the porous structure 150 alone can have a release rate index that is between about 0.06 mm to about 0.1 mm. In other implementations, the porous structure 150 alone can have a release rate index as low as 0.002 and as a high as 0.15. The porous structure 150 having a barrier layer 155 can have a release rate index that is between about 0.06 mm to about 0.1 mm. In still further implementations, the release rate index of the porous structure 150 in the presence of the barrier layer 155 may be significantly different compared to the release rate index of the porous structure 150 alone, but certain parameters of the porous structure 150 can be optimized to achieve the desired release rate index in the presence of the barrier layer 155. For example, the porous structure 150 may be selected based on a greater porosity or a smaller tortuosity or smaller thickness or a combination thereof.

Figure 4C:
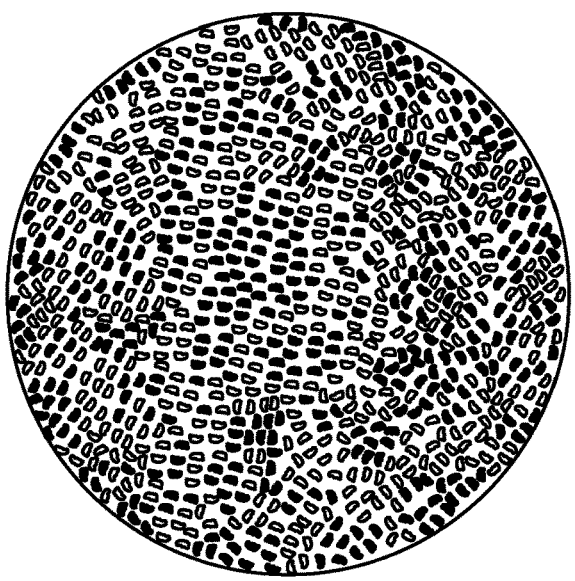
FIG. 4C shows a view of a porous structure configured for sustained release with an implantable device having a 20 micron coating as a barrier layer on the porous structure.
Figure 4B:
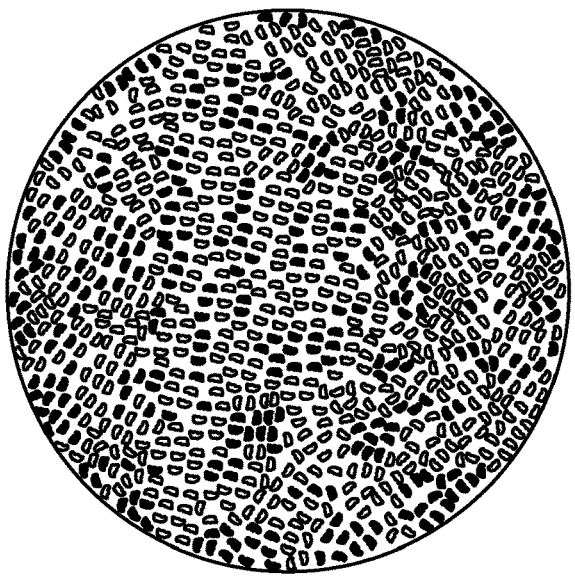
FIG. 4B shows a view of a porous structure configured for sustained release with a therapeutic device having a 10 micron coating as a barrier layer on the porous structure.
Figure 4A:
FIG. 4A shows a View of a porous structure configured for sustained release with a therapeutic device as described herein.
Figure 4D:
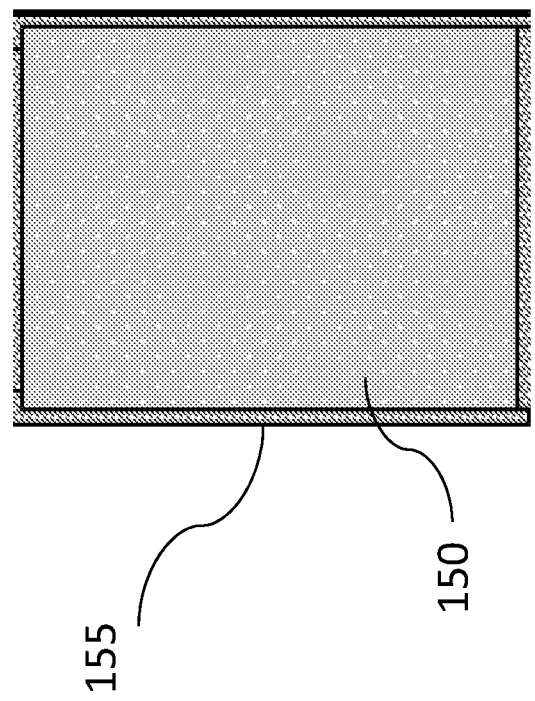
FIG. 4D shows a schematic view of a porous structure configured for sustained release with an implantable device having a coating as a barrier layer on the porous structure.

It should be appreciated that the ranges provided herein are examples and that one or more characteristics can be modified and/or optimized to achieve a desired effect in drug delivery. For example, a porous structure 150 alone prior to combining with a barrier layer 155 can be selected based on its gas flow rate. The gas flow rate can vary, for example, between about 10 standard cubic centimeters per minute (sccm) to about 250 sccm. The gas flow rate can be between 1.5 sccm and 320 sccm. In some implementations, the gas flow rate can be 10, 20, 30, 40, 50, 60, 70, 80, 90, 100, 110, 120, 130, 135, 140, 145, 150, 200, 250, or 400 sccm. The release rate index (mm) of the porous structure 150 alone can be about 0.01 to about 0.10, or from about 0.06 to about 0.04, or from about 0.002 to about 1.5. Generally, the mean pore size of the barrier layer 155 is equal to or less than 0.2 um approaching the size of the drug molecule being delivered. The mean pore size of the porous structure 150 can be increased relative to the mean pore size of the barrier layer 155. For example, the mean pore size of the porous structure 150 can be between about 0.2 microns to about 9 microns. The thickness of the porous structure 150 and the barrier layer 155 can vary as well. The porous structure 150 can have a thickness that is between about 70 microns to about 5000 microns and an outer diameter between about 700 microns to about 1200 microns. The barrier layer 155 can have a thickness that is significantly less than the porous structure 150. In some implementations, the barrier layer 155 is a coating and can have a thickness on the order of a few nanometers up to about 250 microns. The barrier layer 155, whether a coating deposited on the surface as shown in FIG. 4D or a discrete structure in series with the porous structure 150, eau have a minimal thickness so as to maintain effectively the same thickness (length L) of the porous structure 150 alone. In some implementations, the barrier layer 155 can be a filter membrane having a nominal thickness of between about 10 um to about 200 um, or between about 110 um to about 150 um. In some implementations, the combination of the barrier layer 155 and the porous structure in series (e.g. a "composite" release control element) can have a thickness that is greater than a thickness of the porous structure alone while having a minimal impact on the drug diffusion characteristics of the porous structure. Alternatively, the diffusion properties of the porous structure 150 can be adjusted in order to remove any actual or incidental impact caused by the barrier layer 155 on drug release through the porous structure.

As described above with respect to the porous structure 150, the barrier layer 155 can be designed to have a pore size that retains or inhibits passage of molecules, cells, or solid particles of a certain size range and allows for passage of molecules, cells, or solid particles of another size range through the barrier layer 155.

The barrier layer 155 may be described herein as having an average pore size or void space dimension or molecular weight cut off to define the utility of the barrier layer 155 for allowing a molecule to substantially pass through the barrier layer 155 or to substantially limit or prevent a molecule from passing through the barrier layer 155. As such, the molecules of a particular size range (e.g. therapeutic agent) can pass from one side of the barrier layer 155 to another side of the barrier layer 155 such that they are released from the reservoir.

In some implementations, the porous structure 150 can be between Media Grade 0.2 and Media Grade 0.5 porous material and the barrier layer 155 can be a mass of particles having an average particle size of 50 nanometers to 350 nanometers. In some implementations, the porous structure 150 can include 316L stainless steel substrate (Mott Corporation) and the barrier layer 155 can be a mass of particles that are predominantly stainless steel. The porous substrate and the mass of particles can be sintered. In some implementations, a suspension of sinterable particles in a carrier fluid is applied as a barrier layer 155 to the substrate 150 using an ultrasonic spray nozzle and the sinterable particles sintered to the substrate 150 in an ultrasonic spray deposition process. The suspension of particles can be a suspension of particles that are applied to the porous substrate 150. The porous structure 150 can be manufactured according to the process described in U.S. Patent Application No. 2012/0183799, which is incorporated by reference herein in its entirety. The porous structure 150 can be a substrate having pores with a first mean pore size and the barrier layer 155 can be a coating on at least one surface of the substrate having pores with a second mean pore size. The pore size of the porous structure 150 can be equal to or greater than the second mean pore size. The barrier layer 155 can have a mean pore size effective to capture microbes greater than 0.2 microns as evaluated by Microbial retention ASTM F838-05 or equivalent as described in more detail below.

In other implementations, the porous structure 150 can be a sintered titanium element having a thin film titanium coating deposited by physical vapor deposition (PVD) or Plasma Enhanced Chemical Vapor Deposition (PECVD) (Acree Technologies Inc., Concord, Calif.). In some implementations of the sputtering method of forming the barrier layer 155, a source target such as a titanium target is activated so as to vaporize the target material into the surrounding atmosphere such as a vacuum environment in a plasma plume. The vapor can condense onto one or more surfaces of the porous substrate 150 forming the barrier layer 155 as a thin film. The process can take place in ultra-high vacuum or in the presence of a background gas, such as oxygen. The chamber can include fixturing, such as a rotating basket, inside the chamber to allow all surfaces of the porous structure 150 to receive a coating forming the barrier layer 155. Alternatively, a single surface of the porous structure 150 can be coated. Energetic Deposition Process (EDP) can also be used to form a barrier layer 155 on the porous structure 150. EDP is characterized by a high ionization rate and higher add-atom energy than PVD, for example, 50%-100% for EDP compared to about 5% ionization rate for PVD. The add-atom energy in sputtering can be between 1 eV to 3 eV, whereas for EDP the add-atom energy can be from about 30 eV to about 100 eV, depending on the material being deposited and the process conditions. Higher ionization potential and energy can generally lead to denser films deposited. Standard sputtering tends to produce coatings that are somewhat porous with columnar morphology, whereas EDP tends to produce non-porous, denser coatings without columnar structures. As described above, the relative thicknesses of the substrate and the coatings can vary. In some implementations, the porous structure 150 can be between about 700 microns to about 5000 microns, or between about 200 microns and about 1300 microns. In some implementations, the barrier layer 155 can be about 1, 2, 3, 4, 5 microns up to about 10 microns thick. In some implementations, the barrier layer 155 can be about 10, about 20, about 30, about 40, about 50, about 60, or about 70 microns thick. In some implementations, the barrier layer 155 can be between about 5 microns to about 40 microns thick.

Therapeutic quantities of the one or more therapeutic agents can pass through the porous structure 150 and the barrier layer 155 of the therapeutic devices described herein for the extended period of time whereas other particles are inhibited from passing through the porous structure and/or the barrier layer. The therapeutic devices described herein can have a porous structure 150 and/or a barrier layer 155 sized to pass the at least one therapeutic agent comprising molecules having a molecular weight of at least about 100 kDa, 75 kDa, 50 kDa, 25 kDa, 10 kDa, 5 kDa, 2.5 kDa, 1 kDa, 500 Daltons (D), 250 D, 200 D, 150 D, or 100 D. A variety of therapeutic agents are considered herein. Table 1 provides representative therapeutic agents that can be delivered and their molecular weights.

The therapeutic devices described herein can have a porous structure 150 and/or a barrier layer 155 sized to inhibit passage of microbes. Microbes can include, but are not limited to, fungi, fungal spores, protists, as well as bacterial cells including *Brevundimonas diminuta, Propionibacterium acnes, Actinomyces* species. *Bacillus cereus, Clostridium, Enterococcus, Escherichia coli, Haemophilus influenza, Klebsiella pneumoniae, Mycobacterium tuberculosis, Neisseria meningitides, Nocardia asteroids, Pseudomonas aeruginosa, Serratia species, Staphylococcus aureus, Staphylococcus epidermidis, Streptococcus pneumoniae, Streptococcus viridans* and others. The therapeutic devices described herein can have a porous structure 150 and/or a barrier layer 155 sized to inhibit passage of immune cells and/or cellular material from the patient into and/or out of the therapeutic device. Immune cells can include, but are not limited to monocytes, lymphocytes, neutrophils, eosinophils, basophils, macrophages, erythrocytes, platelets, and other cells. The therapeutic devices described herein can have a porous structure 150 and/or a barrier layer 155 sized to inhibit passage of any of these unwanted molecules (e.g. microbes, cells, cellular materials) while allowing for passage of the one or more therapeutic agents from the therapeutic device into the eye.

The release rate of therapeutic agent through a porous structure 150 alone, such as a sintered porous metal structure described above, may be described by the following equation: Release Rate=(D P/F) A $(c_R-c_v)$/L, where:

$c_R$=Concentration in reservoir, $c_v$=Concentration outside of the reservoir or in the target body volume, D=Diffusion coefficient of the therapeutic agent in the reservoir solution, P=Porosity of porous structure, F=Channel parameter that may correspond to a tortuosity parameter of channels of porous structure, A=Area of porous structure, L=Thickness (length) of porous structure. Cumulative Release=$1-c_R/c_{R0}=1-\exp((-D\ PA/FL\ V\ R)t)$, where t=time and $V_r$=reservoir volume.

The parameters of the porous structure 150 that affect the passive molecular diffusion of the drug from the reservoir chamber 160 due to the concentration gradient are the porosity (P), tortuosity (T), area (A), and length or thickness (L) of the porous structure 150. These parameters are encompassed by a release rate index (RRI), which can be used to determine the release of the therapeutic agent. The RRI may be defined as (PA/FL), where P is the porosity of the porous structure, A is an effective area of the porous structure, F is a curve fit parameter corresponding to an effective length, and L is a length or thickness of the porous structure 150.

As described above, the grains of material sintered together to form the porous structure 150 can define interconnected channels of void space through the porous structure 150. The channel parameter (F) can correspond to an elongation of the path of the therapeutic agent released through the porous structure 150. The porous structure 150 can include many of these interconnecting channels and the channel parameter (F) can correspond to an effective length that the therapeutic agent travels along the interconnecting channels of the porous structure 150, such as from the reservoir side to the external side of the device 100.

The diffusion coefficient (D) can be estimated by the following equation from the measured value of $D_{BSA,20C}$=6.1 e-7 cm$^2$/s for bovine serum albumin (BSA) in water at 20° C. (Molokhia et al, Exp Eye Res 2008): $D_{TA,37C}=D_{BSA,20C(\eta 20C/\eta 37C)}(MW_{BSA}/MW_{TA})^{1/3}$ where MW refers to the molecular weight of either BSA or the test compound and η is the viscosity of water. Small molecules have a diffusion coefficient (D) similar to fluorescein (MW=330, D=4.8 to 6 e-6 cm$^2$/s from Stay, M S et al. Pharm Res 2003, 20(1), pp. 96-102). For example, the small molecule may comprise a glucocorticoid such as triamcinolone acetonide having a molecular weight of about 435.

The porous structure 150 has a porosity, thickness, channel parameter and a surface area configured to release therapeutic amounts for the extended time. Porosity of the porous structure 150 can be determined from the weight and macroscopic volume or can be measured via nitrogen gas adsorption. As mentioned above, the porous structure 150 can include a plurality of porous structures. The area A used in the above equation may include the combined area of the plurality of porous structures.

The channel parameter (F) may be a fit parameter corresponding to the tortuosity of the channels. For a known porosity (P), surface area (A) and thickness (L) of the surface parameter, the curve fit parameter (F), which may correspond to tortuosity of the channels, can be determined based on experimental measurements. The parameter PA/FL can be used to determine the desired sustained release profile, and the values of P, A, F and L determined. The rate of release of the therapeutic agent corresponds to a ratio of the porosity to the channel parameter, and the ratio of the porosity to the channel parameter can be less than about 0.5 such that the porous structure releases the therapeutic agent for the extended period. For example, the ratio of the porosity to the channel parameter (F) is less than about 0.1 or for example less than about 0.2 such that the porous structure releases the therapeutic agent for the extended period. The channel parameter (F) can be a value of at least about 1, such as at least about 1.2. For example, the value of the channel parameter (F) can be at least about 1.5, for example at least about 2, and can be at least about 5. The channel parameter (F) can be within a range from about 1.1 to about 10, for example within a range from about 1.2 to about 5. The channel parameter (F) to release the therapeutic agent for an intended release rate profile can be determined empirically.

The area (A) in the model originates from the description of mass transported in units of flux; i.e., rate of mass transfer per unit area. For simple geometries, such as a porous disc mounted in an impermeable sleeve of equal thickness, the area (A) corresponds to one face of the disc and the thickness (L) is the thickness of the disc. For more complex geometries, such as a porous structure in the shape of a truncated cone, the effective area (A) can be a value in between the area where therapeutic agent enters the porous structure and the area where therapeutic agent exits the porous structure.

A model can be derived to describe the release rate as a function of time by relating the change of concentration in the reservoir to the release rate described above. This model assumes a solution of therapeutic agent where the concentration in the reservoir is uniform. In addition, the concentration in the receiving fluid is considered negligible ($c_v$=0). Solving the differential equation and rearrangement yields the following equations describing the concentration in the reservoir as a function of time, t, and volume of the reservoir, $V_R$, for release of a therapeutic agent from a solution in a reservoir though a porous structure. $c_R=c_{R0}\exp((-D\ PA/FL\ V_R)\ t)$ and Cumulative Release=$1-c_R/c_{R0}$ The model and determination of parameters in the above equations as well as the tuning of the therapeutic devices to release therapeutic amounts above a minimum inhibitory concentration for an extended time based on bolus injections of the therapeutic agent are described in more detail, for example, in U.S. Pat. No. 8,399,006, which is incorporated by reference herein.

Release rates of a therapeutic agent from the therapeutic devices can be assessed by measuring diffusion of size-matched molecules in vitro through a porous structure over an extended period of time. For example, solutions of BSA or fluorescein or other molecules representative of a drug of interest and having a known concentration can be used to till a reservoir chamber of a therapeutic device and allowed to diffuse over time from the reservoir through a porous structure coupled to the device. The diffusion experiments can be continued for 1, 2, 3, 4, 5, 6, 7, 8, 9, 10 or more weeks and samples collected at various time-points throughout to assess release rate of the therapeutic agent through the porous structure. The samples allow for plotting the cumulative amount of drug released from the device over time. The amount of test molecule within the reservoir chamber and/or outside the reservoir chamber can be measured as is known in the art, for example, by absorbance, fluorescence, ELISA, and other tests.

The measured release rates can be compared to predicted release rates using the model described above relating to the change in concentration in the reservoir to the release rate from the reservoir based upon Fick's Law of Diffusion. As described in U.S. Pat. No. 8,399,006, the release from the device agrees with the trend predicted by the model.

The porosity P can be determined by nitrogen adsorption and is typically provided by the manufacturer along with the area A and length L. The measured cumulative release of a molecule through the porous structure and a prediction from the model describing release through the porous structure can be used to determine the channel parameter F. Thus, upon determination of the channel parameter F, the release rate index (RRI) can be determined. The RRI is determined by fitting the rate data from a device. The determined RRI can be used to determine the release of the therapeutic agent, and the porous structure can be further characterized with gas flow as described herein to determine the RRI prior to placement in a patient.

The porous structure can be subjected to a gas flow test to determine the release rate of a therapeutic from the device. These tests can be used with a porous structure positioned on the therapeutic device or before the porous structure is assembled with the therapeutic device, so as to quantify flow through the porous structure of the device. Flow of gas such as oxygen or nitrogen through the porous structure can be measured with a decay time of the gas pressure. The flow rate and RRI can be determined based on the material of the porous structure. The therapeutic agent can be measured through the porous structure or a similar test molecule. The correspondence of the flow rate with a gas to the release rate of the therapeutic agent is determined empirically. In some implementations, a correlation can be made between the "flow" tests, which are dependent upon a pressure gradient and is a forced gas flow and the actual drug release test, which is dependent upon in vitro passive diffusion through the porous structure. The correlation is described in more detail in U.S. Pat. No. 8,399,006, which is incorporated by reference herein.

The extended release of therapeutic from the reservoir chamber through the porous structure relies on passive, concentration gradient driven molecular diffusion. To measure this type of extended release directly can be time-consuming and prevents the porous structure from being used again. Thus, testing a porous structure using active pressure gradient response as a substitute for characterizing the passive molecular diffusion mechanism is described. In some implementations, the forced gas flow test involving a pressure gradient can correlate with the drug release test that relies upon passive transport of a therapeutic agent via diffusion from the reservoir chamber through the tortuous interconnected channels of the porous structure into the target volume.

The testing described herein and also in U.S. Pat. No. 8,399,006 allows for testing that would suggest performance of porous materials relative to a molecular diffusion mechanism. Fick's Law of Molecular Diffusion says that diffusion through a porous element can be described via a linear concentration gradient over the thickness of the element, L, with the diffusion coefficient reduced by a ratio of porosity, P. over tortuosity, T, yielding the equation:

$$V_R * \frac{\partial c_R}{\partial t} = \left(\frac{-DP}{T}\right) * \frac{(c_R - c_V)}{L} * A$$

where cv=drug concentration in the receiver fluid.

The elements of this equation that are specific to the porous structure can be isolated and combined into the RRI. The porous structure controls drug delivery via its macroscopic dimensions, area and thickness, and its microscopic properties, porosity and tortuosity. These four parameters can be grouped into a single parameter referred to as the Release Rate Index (RRI), which has units of length and is as follows:

$$RRI = \frac{PA}{TL}$$

The RRI parameters can correlate for various porous structures with the quick and easy non-destructive gas flow vs. pressure behavior. This allows for 100% QC testing of devices to ensure long-term sustained drug release performance without so much as getting the porous structures wet. This also allows for intelligent selection of porous structures not currently in inventory based on interpolation of the correlation. Further, the RRI curves and an understanding of device properties (e.g. reservoir volume capacity) and drug properties (e.g. drug concentration and drug molecular diffusivity), allow for one to project the release behavior of systems that are not yet built. This correlation allows for projections of a variety of drug release parameters that may be of interest such as daily release rates over time, estimated resultant concentrations in the target volume, cumulative amounts or percent of amount of drug released, as well as forecasting expected duration of efficacy for a known therapeutic dose requirement.

Figure 6:
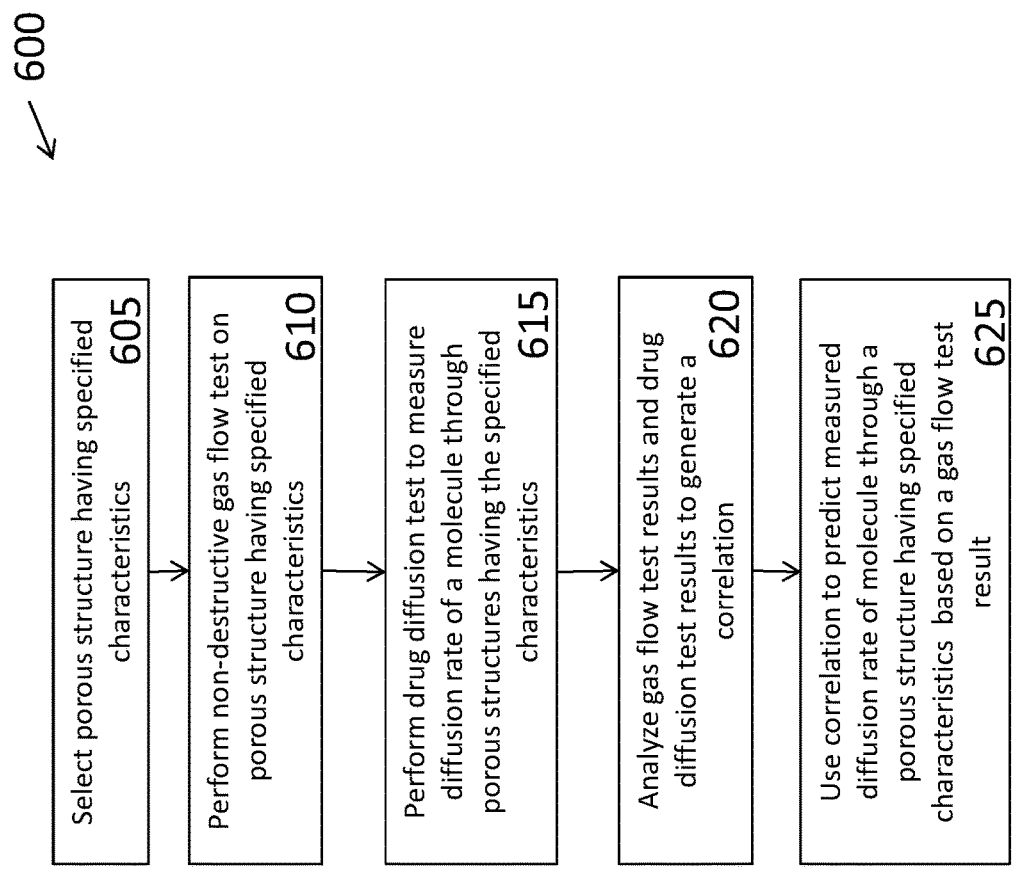
FIG. 6 is a flow chart demonstrating a method of manufacturing a therapeutic device with a porous structure configured for sustained release of a therapeutic agent.

FIG. 6 is a flow chart demonstrating a method of manufacturing 600 a therapeutic device with a porous structure configured for sustained release of a therapeutic agent. It should be appreciated that the steps described need not be performed exactly in the order shown. A porous structure 150 having specified characteristics can he selected (box 605). The specified characteristics or parameters can include characteristics that impact drug diffusion rate through the porous structure such as material type, solid particle size retained, porosity P, area A, length or thickness L, mean pore size, and the like. The specified characteristics are encompassed by a release rate index (RRI), which can be used to determine the release of the therapeutic agent. The RRI may be defined as (PA/FL), where F is a curve fit parameter corresponding to an effective length. For example, the porous structure can be a 316L stainless steel substrate having a porosity of between about 10%-20%, a Media Grade of 0.2. a thickness of between about 0.50 mm to about 1.50 mm, and a mean pore size of about 3 um to about 5 um, to upwards of 50 um. A non-destructive gas flow test can be performed on a porous structure having the specified characteristics (box 610) to obtain a performance result. For example, the performance result can be a gas flow rate of about 100 sccm to about 150 sccm. A drug diffusion test can be performed on a porous structure having the specified characteristics to measure diffusion rate of a molecule through the porous structure (box 615). For example, the measured diffusion rate of bovine serum albumin (BSA) through the porous structure. The measured diffusion rate of the molecule through the porous structure allows for the RRI to be calculated. The data from the non-destructive gas flow tests and the destructive gas flow tests can be analyzed to generate a correlation between the two test types (box 620), the correlation being between a pressure gradient, forced gas flow test and an actual drug release test, which is dependent upon passive diffusion through the porous structure. The correlation can be generated using more than one pair of test results. The correlation generated can be used to predict a measured diffusion rate of the molecule through a porous structure having the same specified characteristics based on a test result of the porous structure during a non-destructive gas flow test (box 625). The correspondence of the flow rate with a gas to the release rate of a therapeutic agent is thus determined empirically. Thus, the porous structure 150 can be subjected only to a non-destructive test and a prediction made as to the result that would be achieved by performing a destructive test so as to quantify diffusion of drug through the porous structure. When the porous structure 150 is coated as described herein or is combined with a barrier layer such as a discrete filter membrane positioned adjacent the porous structure 150 the predictions with regard to diffusion of drug through the porous structure based on the non-destructive test result remain accurate.

The effects of the barrier layer on drug diffusion, whether the barrier layer is a coating or a discrete filter membrane positioned in series with the porous structure, can be minimal. Thus, the method of manufacturing described above can be applicable whether the barrier layer is used or not.

The therapeutic devices described herein can be implanted for as long as is helpful and beneficial to the patient. For example the device can be implanted for at least about 1 year, 2 years, 3 years, 4 year, 5 years and up to permanently for the life of the patient. Alternatively or in combination, the device can be removed when no longer helpful or beneficial for treatment of the patient. In other implementations, the device can be implanted for at least about 4 ears to 10 years, for example a duration of treatment period for a chronic disease such as diabetic macular edema or age-related macular degeneration. The device can be periodically refilled in the physician's office with new therapeutic agent as indicated by disease progression. For diseases such as age-related macular degeneration, the device can be refilled as frequently as once every week, bi-weekly, monthly, bi-monthly, every 3 months, every 4 to 6 months, every 3 to 9 months, every 12 months, or any other period as indicated to treat a disease.

It should be appreciated that a variety of diseases and/or conditions can be treated with the devices and systems described herein, for example: glaucoma, macular degeneration, retinal disease, proliferative vitreoretinopathy, diabetic retinopathy, uveitis, keratitis, cytomegalovirus retinitis, cystoid macular edema, herpes simplex viral and adenoviral infections and other eye diseases, eye infections (including, but not limited to, infections of the skin, eyelids, conjunctivae, and/or lacrimal excretory system), orbital cellulitis, dacryoadenitis, hordeolum, blepharitis, conjunctivitis, keratitis, corneal infiltrates, ulcers, endophthalmitis, panophthalmitis, viral keratitis, fungal keratitis herpes zoster ophthalmicus, viral conjunctivitis, viral retinitis, uveitis, strabismus, retinal necrosis, retinal disease, vitreoretinopathy, diabetic retinopathy, cytomegalovirus retinitis, cystoids macular edema, herpes simplex viral and adenoviral injections, scleritis, mucormycosis, canaliculitis, acanthamoeba keratitis, toxoplasmosis, giardiasis, leishmanisis, malaria, helminth infection, etc. It also should be appreciated that medical conditions besides ocular conditions can be treated with the devices and systems described herein. For example, the devices can deliver drugs for the treatment of inflammation, infection, cancerous growth. It should also be appreciated that any number of drug combinations can be delivered using any of the devices and systems described herein.

The devices described herein can be used to deliver agent or ants that ameliorate the symptoms of a disease or disorder or ameliorate the disease or disorder including, for example, small molecule drugs, proteins, nucleic acids, polysaccharides, biologics, conventional drugs and drug therapies, including vaccines, which are known to those skilled in the art. Examples of therapeutic agents suitable for use in accordance with embodiments of the therapeutic devices described herein are listed throughout as well as in Table 1.

Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Exemplary therapeutic agents include, for example, cytokines, growth factors, proteins, peptides or peptidomimetics, bioactive agents, photosensitizing agents, radionuclides, toxins, anti-metabolites, signaling modulators, anti-cancer antibiotics, anti-cancer antibodies, angiogenesis inhibitors, radiation therapy, chemotherapeutic compounds or a combination thereof The drug may be any agent capable of providing a therapeutic benefit. In an embodiment, the drug is a known drug, or drug combination, effective for treating diseases and disorders of the eye. In non-limiting, exemplary embodiments, the drug is an antiinfective agent (e.g., an antibiotic or antifungal agent), an anesthetic agent, an anti-VEGF agent, an anti-inflammatory agent, a biological agent (such as RNA), an intraocular pressure reducing agent (i.e., a glaucoma drug), or a combination thereof Non-limiting examples of drugs are provided below.

The therapeutic agent can include a macromolecule, for example an antibody or antibody fragment. The therapeutic macromolecule can include a VEGF inhibitor, for example commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ Avastin™, Macugen™, and VEGF Trap. The therapeutic agent can include small molecules such as of a corticosteroid and analogues thereof. For example, the therapeutic corticosteroid can include one or more of trimacinalone, trimacinalone acetonide, dexamethasone, dexamethasone acetate, fluocinolone, fluocinolone acetate, or analogues thereof. Alternatively or in combination, the small molecules of therapeutic agent can include a tyrosine kinase inhibitor comprising one or more of axitinib, bosutinib, cediranib, dasatinib, erlotinib, gefitinib, imatinib, lapatinib, lestaurtinib, nilotinib, semaxanib, sunitinib, toceranib, vandetanib, or vatalanib, for example. The therapeutic agent can include an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™), axitinib, or pazopanib. The therapeutic agent can include a therapeutic agent suitable for treatment of dry AMD such as one or more of Sirolimus™ (Rapamycin), Copaxone™ (Glatiramer Acetate), Othera™, Complement C5aR blocker, Ciliary Neurotrophic Factor, Fenretinide or Rheopheresis. The therapeutic agent can include a therapeutic agent suitable for treatment of wet AMD such as one or more of REDD14NP (Quark), Sirolimus™ (Rapamycin), ATG003; Regeneron™ (VEGF Trap) or complement inhibitor (POT-4), complement factor D inhibitors. The therapeutic agent can include a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), soratenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/NEGFR2, small molecule commercially available from Esai, Co.).

The therapeutic agent can include inhibitors of VEGF receptor kinase; inhibitors of VEGFA, VEGFC, VEGFD, bFGF, PDGF, VEGF/PDGF, VEGFA/Ang2, Ang-2, PDGFR, cKIT, FGF, BDGF, BDGFNEGF/FGF, mTOR, $\alpha v \beta 3$, $\alpha v \beta 5$, $\alpha 5 \beta 1$ integrins, $\alpha v \beta 3/\alpha v \beta 5/\alpha 5 \beta 1$ integrins, alpha2 adrenergic receptor; inhibitors of complement factor B (e.g. TA106), inhibitors of complement factor D (CFD) (Lampalizumab/TNX-234), inhibitors of C3 (e.g. APL-2, novel compstatin analogs), inhibitors of C5 (e.g. Eculizumab, Zimura, ARC1905, ALN-CC5), inhibitors of C5a (e.g. JPE-1375), and related targets; tubulin; AAV-CD56. The therapeutic agent can also include Complement Factor II (CFII), engineered inini-CFH, or recombinant CFH (rCFH).

A variety of therapeutic agents can be delivered using the drug delivery implants described herein, including: anesthetics, analgesics, cell transport/mobility impending agents such as colchicine, vincristine, cytochalasin B and related compounds; antiglaucoma drugs including beta-blockers such as timolol, betaxolol, atenolol, and prostaglandins, lipid-receptor agonists or prostaglandin analogues such as bimatoprost, travoprost, latanoprost, unoprostone etc; alpha-adrenergic agonists, brimonidine or dipivefrine, carbonic anhydrase inhibitors such as acetazolamide, methazolamide, dichlorphenamide, diamox; and neuroprotectants such as nimodipine and related compounds.

Additional examples include targets affecting angiopoietin and angiopoietin receptors that bind angiopoietin including, but not limited to TIE-1, TIE-2, Ang1, Ang2, Ang3, Ang4, including but not limited to pazopanib (Votrient) or any other therapeutic described in US Publication No. 2014/0276482 and PCT Application Ser. No. PCT/US2015/043921, which are each incorporated by reference herein.

Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericin B, ketoconazole, and related compounds; anti-viral agents such as trifluorothymidine, acyclovir, ganciclovir, DDI, AZT, foscamet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics, muscarinics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators; Ranibizumab, Bevacizamab, and Triamcinolone.

Antiinflammatories, such as non-steroidal anti-inflammatories (NSAIDs) may also be delivered, such as cyclooxygenase-1 (COX-1) inhibitors (e.g., acetylsalicylic acid, for example ASPIRIN from Bayer AG, Leverkusen, Germany; ibuprofen, for example ADVIL from Wyeth, Collegeville, Pa.; indomethacin; mefenamic acid), COX-2 inhibitors (CELEBREX from Pharmacia Corp., Peapack, N.J.; COX-1 inhibitors), including a prodrug NEPAFENAC; immunosuppressive agents, for example Sirolimus (RAPAMUNE, from Wyeth, Collegeville, Pa.), or matrix metalloproteinase (MMP) inhibitors (e.g., tetracycline and tetracycline derivatives) that act early within the pathways of an inflammatory response. Anticlotting agents such as heparin, antifibrinogen, fibrinolysin, anti clotting activase, etc., can also be delivered.

Antidiabetic agents that may be delivered using the disclosed implants include acetohexamide, chlorpropamide, glipizide, glyburide, tolazamide, tolbutamide, insulin, aldose reductase inhibitors, etc. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotanc, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, steroids, nucleic acids, saccharides, lipids, glycolipids, glycoproteins, and other macromolecules can be delivered using the present implants. Examples include: endocrine hormones such as pituitary, insulin, insulin-related growth factor, thyroid, growth hormones; heat shock proteins; immunological response modifiers such as muramyl dipeptide, cyclosporins, interferons (including $\alpha$, $\beta$, and $\gamma$ interferons), interleukin-2, cytokines, FK506 (an epoxy-pyrido-oxaazcyclotricosine-tetrone, also known as Tacrolimus), tumor necrosis factor, pentostatin, thymopontin, transforming factor bcta2, crythopoetin, antineogenesis proteins (e.g., anti-VEGF, Interferons), among others and anticlotting agents including anticlotting activase. Further examples of macromolecules that can be delivered include monoclonal antibodies, brain nerve growth factor (BNGF), ciliary nerve growth factor (CNGF), vascular endothelial growth factor (VEGF), and monoclonal antibodies directed against such growth factors. Additional examples of immunomodulators include tumor necrosis factor inhibitors such as thalidomide.

In addition, nucleic acids can also be delivered wherein the nucleic acid may be expressed to produce a protein that may have a variety of pharmacological, physiological or immunological activities. Thus, the above list of drugs is not meant to be exhaustive. A wide variety of drugs or agents may be used with the devices described herein, without restriction on molecular weight, etc.

Other agents include anti-coagulant, an anti-proliferative, imidazole antiproliferative agent, a quinoxaline, a phsophonylmethoxyalkyl nucleotide analog, a potassium channel blocker, and/or a synthetic oligonucleotide, 5-[1-hydroxy-2-[2-(2-methoxyphenoxyl) ethylamino]ethyl]-2-methylbenzenesulfonamide, a guanylate cyclase inhibitor, such as methylene blue, butylated hydroxyanisole, and/or N-methylhydroxylamine, 2-(4-methylaminobutoxy) diphenylmethane, apraclonidine, a cloprostenol analog or a fluprostenol analog, a cross linked carboxy-containing polymer, a sugar, and water, a non-corneotoxic serine-threonine kinase inhibitor, a nonsteroidal glucocorticoid antagonist, miotics (e.g., pilocarpine, carbachol, and acetylcholinesterase inhibitors), sympathomimetics (e.g., epinephrine and dipivalylepinephxine), beta-blockers (e.g., betaxolol, levobunolol and timolol), carbonic anhydrase inhibitors (e.g., acetazolamide, methazolamide and ethoxzolamide), and prostaglandins (e.g., metabolite derivatives of arachidonic acid, or any combination thereof.

Additional examples of beneficial drugs that may be employed and the specific conditions to be treated or prevented are disclosed in Remington, supra; The Pharmacological Basis of Therapeutics, by Goodman and Gilman, 19th edition, published by the MacMillan Company, London; and The Merck Index, 13th Edition, 1998, published by Merck & Co., Rahway, N.J., which is incorporated herein by reference.

EXAMPLES

Example 1

Gas Flow Test of Porous Structures With and Without a Barrier Layer

As described above, the RRI parameter is a conjunction of the parameters of the porous element that affect molecular diffusion rates per Fick's Law of Molecular Diffusion. Specifically, RRI=PA/TL where: P=porosity, A=Surface area, T=Tortuosity, L=Length. The addition of a barrier layer having decreased porosity and providing additional thickness to the porous structure was expected to cause a decrease in the release rate and/or affect the correlation between the gas flow test and the diffusion test.

The porous structures tested varied. In some tests, the porous structure were 316L stainless steel sintered substrates (Mott corporation) and the barrier layer was a coating on the porous structure. The substrates were coated by a particle coating and compared to uncoated controls from the same lot. The substrates were 0.2 Media Grade according the measurements of bubble point. The particle coating included a mass of predominantly stainless steel particles formed as described in U.S. 2012/0183799, which is incorporated by reference herein. The particles were nano-particles. The pore size of the coating was <0.2 um in order to provide anti-bacterial protection and considerably smaller than the pore size of the "naive" uncoated substrates.

In other tests, the porous structure included titanium sintered release control elements (RCEs) (Acree Technologies, Inc., Concord, Calif.) and the barrier layer was a coating on the porous structure. The RCEs were coated by a particle coating and compared to uncoated controls from the same lot. The particle coating was performed by Plasma Enhanced Chemical Vapor Deposition (PECVD), using Cathodic Arc, Magnetron Sputtering, and HiPIMS technologies as is known in the art. The particles were nano-particles. The pore size of the coating was <0.2 um in order to provide anti-bacterial protection and considerably smaller than the pore size of the "naïve" uncoated RCEs. The target coating was between about 10um to about 40 um.

In still further tests, the barrier layer was a discrete filter membrane positioned adjacent a surface of the sintered substrate. The membrane was a 0.2 uM PES filter.

The gas flow tests were performed and combined with RRI so as to determine the release profile of the substrates. Each test was performed on the porous substrate with the barrier layer prior to mounting it on a therapeutic device. The porous substrate with the barrier layer test specimen were mechanically connected to the test hardware. A controllable source of a working fluid such as nitrogen or air was coupled to the test hardware to deliver the working fluid. A manometer or other pressure measurement device as well as one or more transducers was used to measure pressure, flow, etc. within the test system. The source pressure was constantly regulated to a known pressure and the flow of the working fluid allowed to flow through a mass flow meter and then through the fixture porous substrate test specimen. The specific characteristics of the porous substrate specimen determined the rate at which the working fluid flowed through the system. Pressure at the open end of the fixture test specimen was regulated to control the back-pressure and therefore the pressure drop across the specimen. A regulated compressed cylinder supplied the test system with a constant source pressure of 30 psig and a constant back pressure of 1 psig. The test fluid flowed through the test specimen at a characteristic rate dependent on the pressure as measured by the mass flow meter. Generally the range was between 10-100 standard cubic centimeters per minute (sccm). The gas flow test was relatively instantaneous in nature. Flow through a test specimen stabilized quickly allowing for a large number of samples to be performed in a rapid fashion.

The results of the gas flow tests were analyzed showing gas flow (sccm) as a function of RRI (mm). The release rate index of the porous structures with the barrier layer were compared to the uncoated control RCEs. Similarly, the gas flow performance of the porous structures with the barrier layer were compared to the controls having no barrier layer.

Example 2

Drug Diffusion Through Porous Structures With and Without a Barrier Layer

The porous structures were used to construct therapeutic devices or device prototypes suitable for characterization of drug release behavior by measuring drug diffusion as described herein. To construct the device prototypes, the reservoirs were fabricated from syringes and porous structures, which can be the same porous structures used in the gas flow tests described above. The porous structures (referred to as RCEs) were press-fit into sleeves machined from Delrin. The sleeves were exposed on one entire planar face to the solution in the reservoir and the other entire planar face to the receiver solution in the vials. The tips were cut off of 1 mL polypropylene syringes and machined to accept a polymer sleeve with an outer diameter slightly larger than the inner diameter of the syringe. The porous RCE/sleeve was press-fit into the modified syringe. In some tests, the barrier layer was a 0.2 uM PES filter membrane mounted above the porous structure, A solution was prepared containing 300 mg/mL BSA (Sigma, A2153-00G) in PBS (Sigma, P3813). Solution was introduced into the therapeutic device, or if syringe prototypes were used into the syringes by removing the piston and dispensing approximately 200 ul into the syringe barrel. Bubbles were tapped to the top and air was expressed out through the RCE. The BSA solution was expressed through the RCE until the syringe held 100 uL as indicated by the markings on the syringe. The expressed BSA solution was wiped off and then rinsed by submerging in PBS. The reservoirs were then placed into 4 mL vials containing 2 mL PBS at room temperature. Collars cut from silicone tubing were placed around the syringe barrels to position the top of the reservoir to match the height of PBS. The silicone tubing fit inside the vials and also served as a stopper to avoid evaporation. At periodic intervals, the reservoirs were moved to new vials containing PBS. The amount of BSA transported from the reservoir through the RCE was determined by measuring the amount of BSA in the vials using a BCA™ Protein Assay kit (Pierce, 23227).

The cumulative amount released into the vials were measured over time. The percent of cumulative release of BSA through the RCEs were measured at 1 week, 2 weeks, 3 weeks, 4 weeks and beyond. The percent cumulative release of the RCEs with a barrier layer were compared to the controls having no barrier layer to assess whether there was an impact on drug release. Gas flow and pressure decay tests were used to identify specified characteristics of the RCEs that may be correlated to other test results such as chemical or pharmacologic performance.

Example 3

Microbial Retention Testing

Porous structures with a barrier layer were tested for their ability to remove microbes from a liquid or gas medium and compared to porous structures having no barrier layer. Generally, to remove microbes such as bacterial cells from a liquid or gas medium a pore size of approximately 0.2 microns or less is needed. Porous structures prepared as described above were tested for their effectiveness to remove bacteria by using Microbial Retention ASTM F838-05 or equivalent. For microbial retention testing per ASTM F838-05, all equipment was sterilized/disinfected prior to use. All testing was conducted in a laminar flow hood. Each porous structure, including those having a barrier coating and those not having a barrier coating, were prepared by filtering a minimum of 100 mL of sterile buffer through it as a control. One hundred milliliters of filtrate was aseptically collected downstream of the controls in a sterile container. The filtrate was filtered using microbial retentive filters. The microbial retentive filters were placed onto Plate Count Agar and allowed to incubate at 30±2° C. for 7 days. A 48 hour pre-count was performed on each filter. It should be appreciated that other microbial retention tests are contemplated herein. For example, microbial retention can be tested in a way that does not involve forced flow through the container. For example, tests can be performed to assess effectiveness of a container to inhibit bacterial infiltration upon immersion similar to the diffusion test set-up.

After the controls were processed, each porous structure were challenged with approximately $3 \times 10^7$ to $5 \times 10^7$ CFU/100 mL of $B.$ $diminuta$. One hundred milliliters of filtrate were aseptically collected downstream of the porous structures in a sterile container. The filtrate was filtered using a microbial retentive filter. The microbial retentive filter was placed onto Plate Count Agar and allowed to incubate at 30±2° C. for 7 days. A 48 hour pre-count was performed on each filter. Analyzing the colony forming units (CFU)/100 mL provides information regarding which porous structures inhibited bacterial infiltration (pass) and which allowed for bacteria to make its way through the porous structure (fail).

Example 4

Mitigation of Bolus Release Through Porous Structures With and Without a Barrier Layer During initial filling or refilling of a reservoir chamber of a fixed volume therapeutic device there can occur a transient increase in pressure within the reservoir chamber. This increase in pressure within the reservoir chamber can create a pressure gradient across the porous structure that can cause the reservoir solution being delivered to be expressed through the porous structure into the surrounding tissues. The porosity of the porous structure, among other factors (e.g. delivery rate), can affect the magnitude of bolus expressed. Generally, a higher porosity porous structure has a lower pressure drop and a higher bolus is released upon filling.

Figure 5:
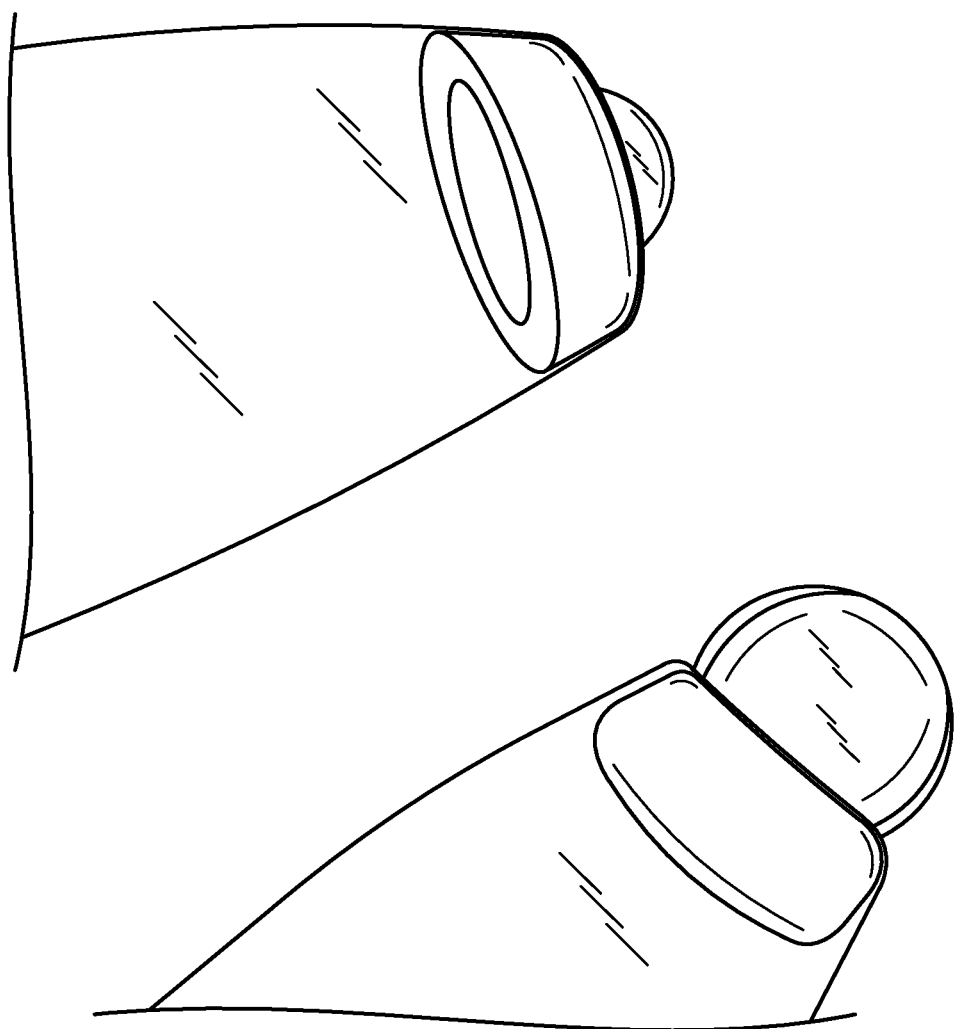
FIG. 5 is a still-frame capture of a video recording of the filling of a therapeutic device having a coated porous structure compared to a therapeutic device having an uncoated porous structure.

A subjective assessment of the impact of the barrier layer on bolus release through the porous structures was conducted. A therapeutic device having a coated RCE and a therapeutic device having an uncoated RCE as described in the examples above were connected to a bifurcated line attached to a single pressure source to simulate filling of the reservoir chamber of the device. FIG. 5 is a still frame capture of a video recording of the filling of the coated RCE (top device) compared to the uncoated control (lower device). The coated RCE significantly inhibited bolus release of fluid through the RCE upon application of a pressure gradient compared to the uncoated control. RCE in combination with a discrete porous structure, such as a PES filter membrane (Sterlitech Corp., Kent, Wash.), also significantly inhibited bolus release of fluid through the RCE upon application of a pressure gradient. Bolus release of therapeutic fluid is associated with an "active" application of a pressure gradient whereas drug release is associated with "passive" concentration gradient driving force. The porous barrier layer having minimal thickness (or length L) has a decreased porosity compared to the porous structure such that drug release via diffusion is negligibly affected but fluid flow via a pressure gradient is more substantially impacted. Thus, the less porous, dense extra layer inhibits the release of a bolus during filling by forming a pressure barrier.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" arc each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

TABLE 1

Therapeutic Agent List

| Generic Name | Brands (Companies) | Category | Indication | Molecular Weight |
|---|---|---|---|---|
| 2-Methoxyestradiol analogs | (Paloma Pharmaceuticals) | Angiogenesis inhibitors | AMD | |
| 3-aminothalidomide | | | | |
| 13-cis retinoic acid | Accutane ™ (Roche Pharmaceuticals) | | | |
| A0003 | (Aqumen BioPharmaceuticals) | A0003 | AMD | |
| A5b1 integrin inhibitor | (Jerin Ophthalmic); (Ophthotech) | nhibitors of a5b1 integrin | AMD | |
| Abarelix | Plenaxis ™ (Praecs Pharmaceuticals) | Anti-Testosterone Agents; Antineoplastic Agents | For palliative treatment of advanced prostate cancer. | 37731 |
| Abatacept | Orencia ™ (Bristol-Myers Squibb) | Antirheumatic Agents | For the second line reduction of the signs and symptoms of moderate-to-severe active rheumatoid arthritis, inducing inducing major clinical response, slowing the progression of structural damage, and improving physical function in adult patients who have | 37697 |
| Abciximab | ReoPro ™; ReoPrc ™ (Centocor) | Anticoagulants; Antiplatelet Agents | For treatment of myocardial infarction. adjunct to percutaneous loronary intervention, unstable angina | 42632 |
| ABT-578 | (Abbot Laboratories) | Limus Immunophilin Binding Compounds | | |
| Acetonide | | | | |
| Adalimumab | Humira ™ (Abbott Laboratories) | Antirheumatic Agents; Immunomodulatory Agents | Uveitis, AMD | 25645 |
| Aldesleukin | Proleukin ™, Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |
| Alteplase | Activase ™ (Gener tech Inc) | Thrombolytic Agents | For management of acute myocardial infarction acute ischemic strok and for lysis of acute pulmonary emboli | 54732 |
| AMG-1470 | | | | |
| Anakinra | Kineret ™ (Amgen nc) | Anti-Inflammatory Agents, Non-Steroidal; Antirheumatic Agents; Immunomodulatory Agents | For the treatment of adult rheumatoid arthritis. | 65403 |
| Anecortave acetate | | | | |
| Angiostatin | | | | |
| Anistreplase | Eminase ™ (Wulfing Pharma GmbH) | Thrombolytic Agents | For lysis of acute pulmonary emboli, intracororary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |
| Anti-angiogeric bifunctional protein | Icon-1 ™ (Iconic Therapeutics) | Anti-angiogeric bifunctional protein, Icon-1 | AMD | |
| Anti-endothelial growth factor | | | | |
| Antihemophilic Factor | Advate ™; Alphanate ™; Bioclate ™; Helixate ™; Helixate FS ™; Hemofil M ™; Humate-P ™; Hyate:C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand diseae and Factor XIII deficiency | 70037 |
| Antithymocyte globulin | Genzyme); Thymoglobulin ™ (SangStat Medical | Immunomodulatory Agents | For prevention of renal transplant rejection | 37173 |
| Anti-hypertensive MC1101 | (MacuCLEAR) | Anti-hypertensive MC1101 | AMD | |
| Anti-platelet devired growth factor | | | | |

TABLE 1-continued

Therapeutic Agent List

| Generic Name | Brands (Companies) | Category | Indication | Molecular Weight |
|---|---|---|---|---|
| Anti-VEGF AP23841 | (Neurotech); Avasin ™ (NeoVista) (Ariad) | Anti-VEGF Limus Immunophilin Binding Compounds | AMD | |
| ARC1905 | Ophthotech | Complement Cascade Inhibitor (Factor C5) | | |
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who are at an increased risk for blood loss and blood transfusio | 90569 |
| Arcitumomab | CEA-Scan ™ | Diagnostic Agents; Imaging Agents | For imaging colorectal tumors | 57561 |
| Asparaginase | Elspar ™ (Merck & Co. Inc) | Antineoplastic Agents | For treatment of acute lympocytic leukemia and non-Hodgkins lymphoma | 132.118 |
| Axitinib | | Tyrosine Kinase Inhibitors | | 386 |
| Basiliximab | Simulec ™ (Novaris Pharmaceuticals) | Immunomodulatory Agents; Immunosuppressive Agents | For prophylactic treatment of kidney transplant rejection | 61118 |
| Becaplermin | Regranex ™, Regranex ™ (OMJ Pharmaceuticals) | Anti-Ulcer Agents; Topical | For topical treatment of skin ulcers (from diabetes) | 123969 |
| Bevacizumab | Avastin ™, Avastin ™ (Genentech Inc) | Antiangiogenesis Agents; Antineoplastic Agents | For treatment of metastatic colorectal cancer | 27043 |
| Bivalirudin | Angiomax ™; Angiomax ™ (Medicines Co or MDCO); Angiox ™ | Anticoagulants; Antithrombotic Agents | For treatment of heparin-induced thrombocytopenia | 70037 |
| Bortezomib | | Proteosome Inhibitors | | |
| Bosutinib | | Tyrosine Kinase Inhibitors | | 530 |
| Botulinum Toxin Type A | BOTCX ™ (Allegran Inc); BOTOX Cosmetic ™ (Allegran Inc); Botox ™; Dysport ™ | Anti-Wrinkle Agents; Antidystonic Agents; Neuromuscular Blocking Agents | For the treatment of cervical dystonia in adults to decrease the severity of abnormal head position and neck pain associated with cervical dystonia. Also for the treatment of severe primary axillary hyperhidrosis that is inadequately managed with topical | 23315 |
| Botulinum Toxin Type B | Myobloc ™ (Solstice Neurosciences); Neurobloc ™ (Solstice Neuro sciences) | Antidystonic Agents | For the treatment of patients with cervical cystonia to reduce the severity of abnormal head position and neck, pain associated with cervical cystonia. | 12902 |
| C5 inhibitor | (Jerini Ophthalmic; (Ophthotech) | Inhibitors of C5 | AMD | |
| Cal101 | Calistga | PI3Kdelta Inhibitor | AMD, DME | |
| Canstatin | | | | |
| Capromab | ProstaScint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™, Erbitux ™ (ImClone Systems Inc) | Antineoplastic Agents | For treatment of metastatic colorectal cancer. | 42632 |
| Choriogonadotropin alfa | Novarel ™; Ovidrel ™; Pregnyl ™, Profasi ™ | Fertility Agents; Gonadotropins | For the treatment of female infertility | 78617 |
| Cilary neurotrophic factor | (Neurotech) | Cilary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | NovoSeven ™ (Noro Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ | Anti-Ulcer Agents; Topical | For treatment of chronic dermal ulcers and severe skin burns | 138885 |
| Complement factor H recombinant | (Optherion); (Taligen Therapeutics) | Complement factor H recombinant | AMD, Geographic Atrophy | |

TABLE 1-continued

Therapeutic Agent List

| Generic Name | Brands (Companies) | Category | Indication | Molecular Weight |
|---|---|---|---|---|
| Compstatin derivative peptide, POT-4 | (Potentia Pharmaceuticals) | Complement Factor C3 Inhibitors; Compstatin Derivative Peptides | AMD | |
| Corticotropin | ACTH ™; Acethropan ™; Acortan ™; Actha- ™; Exacthir ™; H.P. Acthar Gel ™: Isactid ™: Purified cortrophin gel ™; Reacthin ™; Solacthyl ™; Tubex | Diagnostic Agents | For use as a diagnostic agent in the screening of patients presumed to have adrenocortical insufficiency. | 33927 |
| Cosyntropin | Cortrcsyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |
| Cyclosporine | Gengraf ™ (Abbott labs); Neoral ™ (Novartis); Restass ™; Restasis ™ (Allergan Inc); Sandimmune ™ (Novartis); Sangoya ™ | Antifungal Agents; Antirheumatic Agents; Dermatologic Agents; Enzyme Inhibitors; Immunomodulatory Agents; Immunosuppressive Agents | For treatment of transplant rejection, rheumatoid arthritis, severe psoriasis | 32953 |
| Daclizumab | Zenapax ™ (Hoffmann-La Roche Inc) | Immunomodulatory Agents; Immunosuppressive Agents | For prevention of renal transplant rejection Uveitis | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |
| Defibrotide | Dasovas ™, Noravid ™, Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatics; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflmmation, macular edema following branch retinal vein occlusion (BRVO) or central retinal vein occlusion (CRVO) | 392 |
| Diclofenac | | Cyclooxygenase Inhibitors | | |
| Dithiocarbamate | | NFκB Inhibitor | | |
| Dornase Alfa | Dilor ™; Dilor-400 ™; Lufyllin ™, Lufyllin-400 ™; Neothylline ™, Pulmozyme ™ (Genentech Inc) | Enzyme Replacement Agents | For the treatment of cystic fibrosis. | 7656 (double strand) |
| Drotrecogin alfa | Xigris ™; Xigris ™, Eli Lilly & Co) | Antisepsis Agents | For treatment of severe sepsis | 267012 |
| Eculizumab | Soliris ™, Soliris ™ (Alexion Pharmaceuticals) | Complement Cascade Inhibitor (Factor C5) | AMD | 188333 |
| Efalizumab | Raptiva ™; Raptiva ™ (Genentech Inc) | immunomodulatory Agents; immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epcmax ™ (Elanex); Eprex ™ (Janssen-Cilag. Ortho Biologies LLC); NeoRecormon ™ (Roche); Procrit ™ (Ortho Biotech); Recormon ™ (Roche) | Antianemic Agents | For treatment of anemia (from renal transplants or certain HIV treatment) | 55066 |

TABLE 1-continued

Therapeutic Agent List

| Generic Name | Brands (Companies) | Category | Indication | Molecular Weight |
|---|---|---|---|---|
| Eptifibatide | Integrilin ™; Integrilin ™ (Millennium Pharm) | Anticoagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Antirheumatic Agents; Immunomodulatory Agents | Uveitis, AMD | 25645 |
| Everolimus | Novartis | Limus Immunophilin Einding Compounds, mTOR | AMD | |
| Exenatide | Byetta ™, Byetta ™ (Amylin/Eli Lilly) | | Indicated as adjunctive therapy to improve glycemic control in patients with Type 2 diabetes mellitus who are taking metformin, a sulfonylurea, or a combination of both, but have not achieved adequate glycemic control. | 53060 |
| FCFD4514S | Genentech/Roche | Complement Cascade Inhibitor (Factor D) | AMD, Geographic Atrophy | |
| Felypressin | Felipresina ™ [INN-Spanish]; Felipressina ™ [DCIT]; Felypressin ™ [USAN:BAN:INN]; Felypressine ™ [INN-French]; Felypressinum ™ [INN-Latin]; Octapressin ™ | Renal Agents; Vasoconstrictor Agents | For use as an alternative to adrenaline as a 10ocalizing agent, provided that local ischaemia is not essential. | 46800 |
| Fenretinide | Sirion/reVision Therapeutics | Binding Protein Antagonist for Oral Vitamin A | AMD, Geographic Atrophy | |
| Filgrastim | Neupogen ™ (Amgen Inc.) | Anti-Infective Agents; Antineutropenic Agents; Immunomodulatory Agents | Increases leukocyte production, for treatmen: in non-myeloid cancer,neutropenia and bone marrow transplant | 28518 |
| FK605-binding proteins, FKBPs | | Limus Immunophilin Binding Compounds | | |
| Fluocinolone Acetonide | Retisert ™ (Bausch & Lomb); Iluvien ™ (Alimera Sciences, Inc.) | Glucocorticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Naglazyme ™; Naglazyme ™ (BioMarin Pharmaceuticals) | Enzyme Replacement Agents | For the treatment of adults and children with Mucopolysaccharidosis VI. | 47047 |
| Gefitinib | | Tyrosine Kinase Inhibitors | | 447 |
| Gemtuzumab ozogamicin | Mylotarg ™, Mylotarg ™ (Wyeth) | Antineoplastic Agents | For treatment of acute myeloid leukemia | 39826 |
| Glatiramer Acetate | Copaxone ™ | Adjuvants, Immunologic; Immunosuppressive Agents | For reduction of the frequency of relapses in patients with Relapsing-Remitting Multiple Sclerosis. | 29914 |
| Glucagon recombinant | GlucaGen ™ (Novo Nordisk); Glucagon ™ (Eli Lilly) | Antihypoglycemic Agents | For treatment of severe hypoglycemia, also used in gastrointestinal imaging | 54009 |
| Goserelin | Zoladex ™ | Antineoplastic Agents; Antineoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |
| Hyaluronidase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Blaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | AMD, DME | 494 |
| Immune globulin | Civacir ™; Flebogamma ™ (Institute Grifols SA); Gamunex ™ (Talecris Biotherapeutics) | Anti-Infectives; Immunomodulatory Agents | For treatment of immunodeficiencies, thrombocytopenic purpura, Kawasaki disease, gammablobulinemia, leukemia, bone transplant | 42632 |
| Infliximab | Remicade ™ (Cenocor Inc) | Immunomodulatory Agents; Immunosuppressive Agents | Uveitis, AMD | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lil); Insulin Lispro (Eli Lily) | Hypoglycemic Agents | For treatment of diabetes (type I and II) | 154795 |

TABLE 1-continued

Therapeutic Agent List

| Generic Name | Brands (Companies) | Category | Indication | Molecular Weight |
|---|---|---|---|---|
| Insulin recombinant | Novolin R ™ (Nove Nordisk) | Hypoglycemic Agents | For treatment of diabetes (type I and II) | 156308 |
| Insulin, porcine | Iletin II ™ | Hypoglycemic Agents | For the treatment of diabetes (type I and II) | 156308 |
| Interferon | | | | |
| Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papiloma Virus | 57759 |
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata 13cuminate. | 57759 |
| Interferon beta-1b | Betaseron™ (Chiron Corp) | Antiviral Agents; Immunomodulatory Agents | For treatment of relapsing/remitting multiple sclerosis | 57759 |
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |
| Mecasermin | Increlex ™; Increlex ™ (Tercica); Iplex | | For the long-term treatment of growth failure in pediatric patients with Primary IGFD or with GH gene deletion who have developed neutralizng antibodies to GH. It is not indicatec to treat Secondary IGFD resulting from GH deficiency, malnutriton, hypoth | 154795 |
| Menotropins | Repronex ™ | Fertility Agents | For treatment of female infertility | 78617 |
| Methotrexate | | Immunomodulatory | Uveitis, DME | |
| mTOR inhibitors | | | | |
| Muromonab | Orthoclone DKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™, Longastatin ™; Sandostatin ™, Sandostatin LAR ™; Sandostatin LAR ™ (Novartis) | Anabolic Agents; Antineoplastic Agents; Hormonal; Gastrointestinal Agents; Hormone Replacement Agents | For treatment of acromegaly and reduction of side effects from cancer chemotherapy | 42687 |
| Omalizumab | Xolair ™ (Genentezh Inc) | Anti-Asthmatic Agents; Immunomodulatory Agents | For treatment of asthma caused by allergies | 29596 |
| Oprelvekin | Neumega ™; Neumega ™ (Genetics Institute Inc) | Coagulants; Thrombotics | Increases reduced platelet levels due to chemotherapy | 45223 |

TABLE 1-continued

Therapeutic Agent List

| Generic Name | Brands (Companies) | Category | Indication | Molecular Weight |
|---|---|---|---|---|
| OspA lipoprotein | LYMErix ™ (SmithKline Beecham) | Vaccines | For prophylactic treatment of Lyme Disease | 95348 |
| OT-551 | (Othera) | Anti-oxidant eyedrop | AMD | |
| Oxytocin | Oxytocin ™ (BAM Biotech); Pitocin ™ (Parke-Davis) Syrtocinon ™ (Sandoz) | Anti-tocolytic Agents; Labor Induction Agents; Oxytocics | To assist in labor, elective labor induction uterine contraction induction | 12722 |
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases casued by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatir-, and irinotecan- containing chemotherapy regimens. | 134279 |
| PDGF inhibitor PEDF (pigment epithelium derived factor) | (Jerini Ophthalmic); (Ophthotech) | Inhibitors of PDGF | AMD | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |
| Pegaspargase | Oncaspar ™ (Enzen Inc) | Antineoplastic Agents | For treatment of acute lymphoblastic leukemia | 132.118 |
| Pegfilgrastim | Neulasta ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Scher ng Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |
| Pegvisomant | Somavert ™ (Pfizer Inc) | Anabolic Agents; Hormone Replacement Agents | For treatment of acromegaly | 71500 |
| Pentoxifylline | | | | |
| Perindozril | | ACE Inhibitors | | |
| Pimecrolimus | | Limus Immunophilin Binding Compounds | | |
| PKC (protein kinase C) inhibitors | | | | |
| POT-4 | Potencia/Alcon | Complement Cascade Inhibitor (Factor C3) | AMD | |
| Pramlintide | Symlin ™; Symlin ™ (Amylin Pharmaceuticals) | | For the mealtime treatment of Type 1 and Type II diabetes in combination with standard insulin therapy, in patients who have failed to achieve adequate glucose control on insulin monotherapy. | 16988 |
| Proteosome inhibitors | Velcade ™ | | Proteosone inhibitors | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (siroliums) | (MacuSight) | Limus Immunophilin Binding Compounds | AMD | |
| Rasburicase | Elitek ™; Elitek ™ (Sanofi-Synthelabo Inc); Fasturtec ™ | Antihyperuricemic Agents | For treatment of hyperuricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |

TABLE 1-continued

Therapeutic Agent List

| Generic Name | Brands (Companies) | Category | Indication | Molecular Weight |
| --- | --- | --- | --- | --- |
| Retinal stimulant | Neurosolve ™ (Vitreoretinal Technologies) | Retinal stimulants | AMD | |
| Retinoid(s) | | | | |
| Rituximab | MabThera ™, Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™, Miacalcin ™ (Novartis) | Antihypocalcemic Agents; Antiosteporotic Agents; Bone Density Conservation Agents | For the treatment of post-menopausal osteoporosis | 57304 |
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SAR 1118 | SARCode | Immunomodulatory Agent | Dry eye, DME, conjunctivitis | |
| SDZ-RAD | | Limus Immunophilin Binding Compounds | | |
| Secretin | SecreFlo ™, Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| SF1126 | Semafore | FI3k/mTOR Inhibition | AMD, DIVE | |
| Sirolimus reformulation (rapamycin) | (MacuSight) | Limus Immunophilin Binding Compounds | AMD | |
| siRNA molecule synthetic, FTP-801i-14 | (Quark Pharmaceuticals) | siRNA molecule synthetic | AMD | |
| Somatropin recombinant | BioTropin ™ (Biotech General); Genotropin ™ (Pfizer); Humatrope ™ (Eli Lilly); Norditroin ™ (Novo Nordisk); Nutropin ™ (Genentech Inc.); NutropinAQ ™ (Genentech Inc.); Protropin ™ (Genentech Inc.); Saizen ™ (Serono SA); Serostim ™; Serostim ™ (Seroro SA); Tev-Tropin ™ (GATE) | Anabolic Agents; Hormone Replacement Agents | For treatment of dwarfism, acromegaly and prevention of HIV-induced weight loss | 71500 |
| Squalamine | | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| TA106 | Taligen | Complement Cascade Inhibitor (Factor B) | AMD | |
| Tacrolimus | | Limus Immunophilin Finding Compounds | | |
| Tenecteplase | TNKase ™ (Genentech Inc) | Thrombolytic Agents | For treatment of myocardial infarction and lysis of intracoronary emboli | 54732 |
| Teriparatide | Apthela ™, Forsteo ™, Forteo ™, Fortessa ™; Opthia ™; Optia ™; Optian ™; Zalectra ™; Zelletra ™ | Bone Density Conservation Agents | For the treatment of osteoporosis in men anc postmenopausal women who are at high risk for having a fracture. Also used to increase bone mass in men with primary or hypogonadal osteoporosis who are at high risk for fracture. | 66361 |

TABLE 1-continued

Therapeutic Agent List

| Generic Name | Brands (Companies) | Category | Indication | Molecular Weight |
|---|---|---|---|---|
| Tetrathiomolybdate | | | | |
| Thalidomide | Celgene | Anti-inflammatory, Anti-proliferative | Uveitis | |
| Thyrotropin Alfa | Thyrogen ™ (Genzyme Inc) | Diagnostic Agents | For detection of residueal or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxa ™ (Corixa Corp) | Antineoplastic Agents | For treatment of non-Hodgkin's lymphoma (CD20 positive, follicular) | 33078 |
| TPN 470 analogue | | | | |
| Trastuzumab | Herceptin ™ (Gerentech) | Antineoplastic Agents | For treatment of HER2-positive pulmonary breast cancer | 137912 |
| Triamcinolone acetonide | Triesence ™ | Glucocorticoid | DME, For treatment of inflammation of the retina | 435 |
| Troglitazone | | Thiazolidinediones | | |
| Tumistatin | | | | |
| Urofollitropin | Fertinex ™ (Seron S.A.) | Fertility Agents | For treatment of female infertility | 78296 |
| Urokinase | Abbokinase ™, Abbokinase ™ (Abbott Laboratores) | Thrombolytic Agents | For the treatment of 22ulmonary embolism, coronary artery thrombosis and IV catheter clearance | 90569 |
| Vandetanib | | Tyrosine Kinase Inhibitors | | 475 |
| Vasopressin | Pitressin ™; Pressyn ™ | Antidiuretics; Oxytocics; Vasoconstrictor Agents | For the treatment of enuresis, polyuria, diabetes insipidus, polydipsia and oesophageal varices with bleeding | 46800 |
| Vatalanib | | Tyrosine Kinase Inhibitors | | 347 |
| VEGF receptor kinase inhibitor | | | | |
| VEGF Trap | Aflibercept ™ (Regneron Pharmaceuticals, Bayer Healthcare AG) | Genetically Engineered Antibodies | DME, cancer, retinal vein occlusion, choroidal neovascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |
| Volociximab | Ophthotech | alpha5beta1 Integrin Inhibitor | AMD | |
| XL765 | Exelix's/Sanofi-Aventis | PI3k/mTOR Inhibition | AMD, DME | |

What is claimed is:

1. A therapeutic device for extended release drug delivery, the device comprising:
 a refillable reservoir configured to receive a therapeutic agent and having an outlet for delivery of the therapeutic agent to a patient from the reservoir;
 a porous structure coupled near the outlet of the reservoir, the porous structure formed of sintered material and configured to control a diffusion rate of the therapeutic agent through the outlet of the reservoir; and
 a barrier layer coupled to the reservoir on or adjacent an inner-facing surface of the porous structure such that the therapeutic agent passes through both the porous structure and the barrier layer upon delivery from the reservoir through the outlet,
 wherein the barrier layer is configured to block passage of contaminants from entering the eye through the porous structure, or is configured to block passage of contaminants from entering the reservoir through the porous structure, or is configured to block passage contaminants from entering the eye and the reservoir through the porous structure,
 and wherein the barrier layer mitigates a bolus release of the therapeutic agent through the porous structure upon an increase in pressure within the reservoir.

2. The therapeutic device of claim 1, wherein the contaminants include one or more of microbes, bacteria, fungal spores, immune cells, and antibodies.

3. The therapeutic device of claim 1, wherein the diffusion rate is controlled by the porous structure so the diffusion rate of the therapeutic agent through the porous structure is unchanged by the presence of the barrier layer.

4. The therapeutic device of claim 1, wherein the porous structure has a mean pore size that is between 3 microns to 50 microns and the barrier layer has a mean pore size that is between 0.01 microns to 0.1 microns.

5. The therapeutic device of claim 1, wherein the barrier layer is a filter membrane formed of a material selected from the group consisting of silver metal, cellulose acetate, ceramic, glass fiber, borosilicate fiber, mixed cellulose ester (MCE), nylon, polyacrylonitrile (PAN), polycarbonate track etch (PCTE), polyethersulfone (PES), polyester track etch (PETE), polypropylene (PP), PTFE, and PVDF.

6. The therapeutic device of claim 1, wherein the sintered material is stainless steel or titanium.

7. The therapeutic device of claim 1, wherein the porous structure has a first mean pore size and the barrier layer has a second mean pore size that is smaller than the first mean pore size so the barrier layer blocks passage of particles having an average particle size within an average particle size range that is outside an average particle size range blocked by the porous structure.

8. The therapeutic device of claim 7, wherein the average particle size range blocked by the barrier layer is greater than 0.01 um.

9. The therapeutic device of claim 7, wherein the average particle size range blocked by the barrier layer is greater than 1 nm.

10. The therapeutic device of claim 7, wherein the second mean pore size is effective to block passage of the particles having the average particle size within the average particle size range, wherein the average particle size range of the barrier layer is equal to or smaller than 0.2 microns and greater than an average particle size range of the therapeutic agent.

11. The therapeutic device of claim 1, wherein the porous structure has a first porosity and the barrier layer has a second porosity, wherein the first porosity is higher than the second porosity, wherein the first porosity is from 16% to 30% and the second porosity is from 1% to 15%.

12. A therapeutic device for extended release drug delivery, the device comprising:
- a refillable reservoir configured to receive one or more therapeutic agents and having an outlet for delivery of the therapeutic agent to a patient from the reservoir;
- a porous structure coupled to the reservoir near the outlet from the reservoir and configured to control a diffusion rate of the one or more therapeutic agents through the outlet of the reservoir, the porous structure formed of sintered material and having a first porosity and a first mean pore size; and
- a barrier layer coupled to the reservoir on or adjacent an inner-facing surface of the porous structure such that the therapeutic agent passes through both the porous structure and the barrier layer upon delivery from the reservoir through the outlet, the barrier layer being a filter membrane having a second porosity and a second mean pore size,
- wherein the first porosity is greater than the second porosity and the first mean pore size is equal to or greater than the second mean pore size.

* * * * *